United States Patent
Kalahasti et al.

(10) Patent No.: US 12,059,491 B2
(45) Date of Patent: *Aug. 13, 2024

(54) COSMETIC COMPOSITION

(71) Applicant: MARY KAY INC., Addison, TX (US)

(72) Inventors: Geetha Kalahasti, Addison, TX (US); Patricia Jacoby, Addison, TX (US); Milagros Sanchez, Addison, TX (US); Shona Burkes-Henderson, Addison, TX (US); David Gan, Addison, TX (US)

(73) Assignee: MARY KAY INC., Addison, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/198,054

(22) Filed: May 16, 2023

(65) Prior Publication Data

US 2024/0009112 A1 Jan. 11, 2024

Related U.S. Application Data

(63) Continuation of application No. 17/849,304, filed on Jun. 24, 2022, now Pat. No. 11,684,566, which is a continuation of application No. 17/117,574, filed on Dec. 10, 2020, now Pat. No. 11,400,043.

(60) Provisional application No. 62/946,120, filed on Dec. 10, 2019.

(51) Int. Cl.
| | |
|---|---|
| A61K 36/00 | (2006.01) |
| A61K 8/67 | (2006.01) |
| A61K 8/92 | (2006.01) |
| A61K 8/9789 | (2017.01) |
| A61K 8/9794 | (2017.01) |
| A61Q 19/08 | (2006.01) |

(52) U.S. Cl.
CPC ............ *A61K 8/9789* (2017.08); *A61K 8/671* (2013.01); *A61K 8/676* (2013.01); *A61K 8/922* (2013.01); *A61K 8/9794* (2017.08); *A61Q 19/08* (2013.01); *A61K 2800/59* (2013.01)

(58) Field of Classification Search
CPC ..................................................... A61Q 19/08
See application file for complete search history.

(56) References Cited

U.S. PATENT DOCUMENTS

| | | | |
|---|---|---|---|
| 4,883,659 A | 11/1989 | Goodman et al. | |
| 5,770,185 A | 6/1998 | Wachter et al. | |
| 6,184,247 B1 | 2/2001 | Schneider | |
| 6,328,987 B1 | 12/2001 | Marini | |
| 6,358,517 B1 | 3/2002 | Pillai et al. | |
| 7,105,184 B2 | 9/2006 | Pauly et al. | |
| 7,531,193 B2 | 5/2009 | Demarne et al. | |
| 7,871,766 B2 | 1/2011 | Pauly et al. | |
| 8,025,907 B2 | 9/2011 | Belfer | |
| 8,057,830 B2 | 11/2011 | Brumbaugh et al. | |
| 8,110,207 B2 * | 2/2012 | Cebrian Puche | A61P 29/00 424/401 |
| 8,609,086 B2 | 12/2013 | Steward et al. | |
| 8,673,375 B2 | 3/2014 | Hill | |
| 8,741,347 B2 | 6/2014 | Laza-Knoerr et al. | |
| 8,815,305 B2 | 8/2014 | Henry et al. | |
| 8,992,953 B2 | 3/2015 | Clavel et al. | |
| 9,044,404 B2 | 6/2015 | Mehta et al. | |
| 9,364,413 B2 | 6/2016 | Lu et al. | |
| 9,844,576 B2 | 12/2017 | Brownell et al. | |
| 9,907,760 B2 | 3/2018 | Auriol et al. | |
| 9,918,931 B2 | 3/2018 | Dersh et al. | |
| 10,010,572 B2 | 7/2018 | Parris | |
| 10,016,474 B2 | 7/2018 | Xie et al. | |
| 10,258,643 B2 | 4/2019 | Utecht et al. | |
| 10,335,364 B2 | 7/2019 | Shrivastava et al. | |
| 10,512,603 B2 | 12/2019 | Alminana Domenech et al. | |
| 2006/0257509 A1 | 11/2006 | Zimmerman et al. | |
| 2008/0069912 A1 | 3/2008 | Demarne et al. | |
| 2012/0288478 A1 | 11/2012 | Florence et al. | |
| 2016/0000094 A1 | 1/2016 | Modak et al. | |
| 2017/0000717 A1 | 1/2017 | Reynoso | |
| 2017/0087082 A1 | 3/2017 | Doering et al. | |
| 2017/0100326 A1 | 4/2017 | Nogueira et al. | |
| 2017/0151172 A1 | 6/2017 | Shrivastava et al. | |
| 2017/0304202 A1 | 10/2017 | Kao et al. | |
| 2017/0367973 A1 | 12/2017 | Tonge et al. | |
| 2018/0042840 A1 | 2/2018 | Alminana Domenech et al. | |
| 2018/0303741 A1 | 10/2018 | Yu et al. | |
| 2019/0167569 A1 | 6/2019 | Ozayman | |
| 2019/0209442 A1 | 7/2019 | Syed et al. | |

(Continued)

FOREIGN PATENT DOCUMENTS

| | | |
|---|---|---|
| CN | 1045536 | 10/1999 |
| CN | 103037838 | 4/2013 |

(Continued)

OTHER PUBLICATIONS

Office Action and Search Report issued in corresponding Chinese Application No. 202080096074.3, dated Dec. 29, 2023 (English Translation provided).
Wang, Jianxin et al. *Collection of Cosmetic Plant Raw Materials*. China Textile Press, 2012, pp. 62, 180, 257-258, and 322-323 (English Translation of relevant parts provided).
*Whitening Cosmetics Science and Technology*, edited by Guanjie Peng and Qingquan Guo, China Light Industry Press Ltd., 2019, Beijing, p. 186 (English Translation of relevant parts provided).
"Argan Oil for Skin: Benefits and Uses for All Skin Types" healthline, Sep. 29, 2018, https://www.healthline.comhealth/argan-oil-for-skin, Accessed Mar. 24, 2021.

(Continued)

*Primary Examiner* — Qiuwen Mi
(74) *Attorney, Agent, or Firm* — NORTON ORSE FULBRIGHT US LLP

(57) ABSTRACT

A method for topically treating skin is disclosed. The method can include applying to skin a composition that includes tetrahexyldecyl ascorbate, *Morus alba* fruit extract, *Acmella oleracea* extract, and retinol, wherein topical application of the composition treats the skin.

14 Claims, 6 Drawing Sheets

(56) References Cited

U.S. PATENT DOCUMENTS

| | | |
|---|---|---|
| 2019/0343907 A1 | 11/2019 | Brown et al. |
| 2020/0000698 A1 | 1/2020 | Woodin et al. |
| 2020/0030252 A1 | 1/2020 | Mata |

FOREIGN PATENT DOCUMENTS

| | | |
|---|---|---|
| CN | 105362148 | 3/2016 |
| CN | 106821849 | 6/2017 |
| CN | 108472220 | 8/2018 |
| CN | 108478484 | 9/2018 |
| CN | 108567594 | 9/2018 |
| CN | 1 09602668 | 4/2019 |
| CN | 110538091 | 12/2019 |
| DE | 69203512 | 3/1996 |
| EP | 0641557 | 3/1995 |
| EP | 2404642 | 1/2012 |
| FR | 2553788 | 4/1985 |
| FR | 2582941 | 10/1987 |
| FR | 2673530 | 5/1995 |
| FR | 2724663 | 3/1996 |
| FR | 3049859 | 10/2017 |
| GB | 2432313 | 6/2008 |
| JP | 2549127 | 10/1996 |
| JP | 2799569 | 9/1998 |
| JP | 3108586 | 11/2000 |
| JP | 3202810 | 8/2001 |
| JP | 3236347 | 12/2001 |
| WO | WO 88/09654 | 12/1988 |
| WO | WO 93/12761 | 7/1993 |
| WO | WO 2017/201597 | 11/2017 |
| WO | WO 2018/004490 | 1/2018 |
| WO | WO 2018/056936 | 3/2018 |
| WO | WO 2018/075810 | 4/2018 |
| WO | WO 2019/083940 | 5/2019 |
| WO | WO 2019/116391 | 6/2019 |
| WO | WO 2019/139214 | 7/2019 |
| WO | WO 2019/145963 | 8/2019 |
| WO | WO 2019/170502 | 9/2019 |

OTHER PUBLICATIONS

"Corneotherapy." Jan. 24, 2016 and California SCC, Barnet.
"EPIDERMIST 4.0: New Skin Builder." Cosmetics Business, Jul. 22, 2013, https://www.cosmeticsbusiness.com/news/article_page_EPIDERMIST_40_New_Skin_Builder/89190. Accessed Oct. 8, 2021.
"Rosemary for your skin" Times of India, Jun. 6, 2017, https://timesofindia.indiatimes.com/life-style/beauty/rosemary-for-your-skin/articleshow/20925095, oms#:-text=The%20anti%%2Dinflammatory%20proporties%20of.including%20dermatitis%2C%20eczama%and%20psoriasis. Accessed Mar. 24, 2021.
"Spotlight On: Galanga Leaf Extract—Does it Really Increase Hyaluronic Acid Production?" FutureDerm, Apr. 23, 2013, https://www.futurederm.com/spotlight-on-gaianga-leaf-extract-does -it-really-increase-hyaluronic-acid-production/. Accessed Mar. 24, 2021.
Benoiderm Efficacy Report. Technical Dossier 12-073GB Oct. 2012, 46 pages.
BV-OSC. Barnet 2009, retrieved from https://lrp-cdn.multisoreensile.com/2d058be6/files/uploaded/POD-BV-OSC%20-%20PROFILE%20(1)/pdf, Accessed Mar. 24, 2021.
Dermofeel enlight: Natural effective whitening blend. drstraetmans intelligence behind beauty 201 5, retrieved from https://www.dr-straetmans.de/dl/media/fillerpublic/5e/b4/5eb406c3-9109-4e61-bb8b-b70e3d571f0b8/fluer_dermofeel_enlight_2015.df, Accessed Mar. 24, 2021.
International Cosmetic Ingredient Dictionary and Handbook, Tenth Edition, CTFA, 2004, vol. 1, p. 139.
International Cosmetic Ingredient Dictionary and Handbook, Tenth Edition, CTFA, 2004, vol. 3, p. 1878.
International Cosmetic Ingredient Dictionary and Handbook, Tenth Edition, CTFA, 2004, vol. 2, p. 1651.
International Cosmetic Ingredient Dictionary and Handbook, Tenth Edition, CTFA, 2004, vol. 2, p. 1641.
International Cosmetic Ingredient Dictionary and Handbook, Tenth Edition, CTFA, 2004, vol. 2, p. 1624.
International Cosmetic Ingredient Dictionary and Handbook, Twelfth Edition, CTFA, 2008, vol. 1, p. 41.
International Cosmetic Ingredient Dictionary and Handbook, Twelfth Edition, CTFA, 2008, vol. 2, p. 1611.
International Search Report and Written Opinion issued in Corresponding PCT Application No. PCT/US2020/070894, dated Apr. 13, 2021.
Klock et al., "Saccharide Isomerate to Deeply Hydrate Skin and Scalp" Cosmetics & Toiletries, Sep. 11, 2013, https://www.cosmeticsandtoiletries.com/formulating/function/delivery/premium-Saccharide-Isomerate-to-Deeply-Hydreate_skin-and-Scalp-223347581.html. Accessed Mar. 24, 2021.
"C-Tango™ Multivitamin Eye Cream—Ingredients" Drunk Elephant, https://www.drunkelephant.com/products-allproducts/products-allproducts-skincare/products-allproducts-skincare-eye-treatments/c-tango%E2%84%A2-multivitamin-eye-cream-850155008013.html. Accessed Jan. 8, 2024.
"C-Tango™ Multivitamin Eye Cream" Drunk Elephant, https://www.drunkelephant.com/products-allproducts/products-allproducts-skincare/products-allproducts-skincare-eye-treatments/c-tango%E2%84%A2-multivitamin-eye-cream-850155008013.html. Accessed Jan. 4, 2024.

* cited by examiner

COSMETIC COMPOSITION

CROSS-REFERENCE TO RELATED APPLICATIONS

This application is a continuation of U.S. application Ser. No. 17/849,304 filed Jun. 24, 2022, which is a continuation of U.S. application Ser. No. 17/117,574 filed Dec. 10, 2020 (now U.S. Pat. No. 11,400,043), which claims the benefit of priority to U.S. Provisional Application No. 62/946,120 filed Dec. 10, 2019. The contents of the referenced applications are incorporated into the present application by reference.

BACKGROUND OF THE INVENTION

Field of the Invention

The present invention relates generally to topical skin compositions and methods that can be used to reduce lines and wrinkles, improve evenness of skin tone, improve elasticity of skin, and/or improve skin barrier function. In particular, the compositions can include plant based materials selected from *Rosmarinus officianalis* leaf extract, *Morus alba* fruit extract, tetrahexyldecyl ascorbate, retinol, *Acmella oleracea* extract, *Alpinia galanga* leaf extract, *Argania spinosa* oil, or saccharide isomerate, or any combination thereof.

Description of Related Art

Ageing, chronic exposure to adverse environmental factors, malnutrition, fatigue, etc., can change the visual appearance, physical properties, or physiological functions of skin and tissue in ways that are considered visually undesirable. Notable and obvious changes include the development of fine lines and wrinkles, loss of elasticity, decreased skin barrier function, increased sagging, loss of firmness, loss of color evenness or tone, coarse surface texture, and mottled pigmentation. Less obvious but measurable changes which occur as skin and tissue ages or endures chronic environmental insult include a general reduction in cellular and tissue vitality, reduction in cell replication rates, reduced cutaneous blood flow, reduced moisture content, accumulated errors in structure and function, alterations in the normal regulation of common biochemical pathways, and a reduction in the skin's and tissue's ability to remodel and repair itself. Many of the alterations in appearance and function of the skin are caused by changes in the outer epidermal layer of the skin, while others are caused by changes in the lower dermis. Regardless of the stimulus for skin damage, when damage occurs, numerous natural and complex biochemical mechanisms are set into motion in attempts to repair the damage.

Extrinsic and intrinsic factors that can damage the skin or tissues are difficult or impossible to avoid. When exposed to some extrinsic factors, when damaged, or through intrinsic factors, the production of structural proteins and proteins involved in elasticity and binding of the skin and tissue can decrease (e.g., elastin, collagen, laminin, and fibronectin). The decrease in such proteins can lead to undesired outcomes such as sagging, decreased firmness, etc. of the skin. Thus, compositions and methods are desired that can firm and condition the skin and/or increase production of elastin, collagen, laminin, and/or fibronectin.

Further, skin-related issues such as lines and wrinkles, unevenness of skin tone, decreased elasticity of skin, and/or lowered skin barrier function can be linked to high antioxidant capacity (TEAC) in skin, decrease in collagen expression, decrease in elastin expression, decrease in laminin expression, increase in matrix metallopeptidase-1 (MMP-1), increase in matrix metallopeptidase-3 (MMP-3), increase in matrix metallopeptidase-9 (MMP-9), increase in pro-inflammatory cytokines (e.g., lipoxygenase, interleukin-6 (TL-6), interleukin-8 (IL-8), tumor necrosis factor (TNF-α), or vascular endothelial growth factor (VEGF)), increase in elastase expression, and/or decrease in fibronectin expression in skin.

Maintaining moisture of the skin helps overcome some unwanted changes in skin. However, maintaining moisture of the skin can be difficult. This is especially true for subjects with skin that is more dry than average (dry skin type). Exposure to chemicals, solvents, washing, cosmetics, fabrics, or dry environments are some of the many ways that skin can lose moisture.

Skin and hair can lose moisture as a result of cleansing and/or freshening the skin and hair. Skin and hair cleansing and/or freshening compositions are typically applied to skin and/or hair and rinsed-off with water (e.g., rinse-off product), robbing the skin of natural oils and lipids. Further, cleansing and freshening compositions oftentimes have ingredients that can be caustic to the surfaces to be cleansed. For instance, many types of cleansers and fresheners use certain surfactants that can cause skin irritation.

Moisturizers are complex mixtures of chemical agents specially designed to make the external layers of the skin (epidermis) softer and more pliable. They increase the skin's hydration (water content) by reducing evaporation. Naturally occurring skin lipids and sterols, as well as artificial or natural oils, humectants, emollients, lubricants, etc., may be part of the composition of commercial skin moisturizers. They usually are available as commercial products for cosmetic and therapeutic uses, but can also be made at home using common pharmacy ingredients. However, moisturizers are not perfect. Some problems associated with moisturizers include unpleasant tactile properties (e.g., heavy, greasy, or sticky feel), instability, skin-irritation, or insufficient moisturization capabilities.

Others have attempted to create compositions and methods that reduce the appearance of fine lines and wrinkles, repair unevenness in skin tone, increase skin elasticity, improve skin barrier function, promote hydration, strengthen and repair skin, and firm and condition skin. However, many attempts have been ineffective, only addressed one or a few of the undesired outcomes, or caused unacceptable side effects themselves, such as skin irritation or an allergic response. As an example, retinol, a retinoid, has been used to reduce fine lines and wrinkles by increasing the production of collagen, used to improve skin color by increasing new blood vessels in the skin, and used to fade age spots and soften skin (Harvard Health Publishing, Healthbeat, "Do retinoids really reduce wrinkles?"). However, retinol is known to cause skin dryness, irritation, and sensitivity to sunlight. Id. Further, not every effective composition will be compatible with every skin or tissue type. Thus, there is a need for new products that are effective at reducing the appearance of fine lines and wrinkles, moisturizing skin, promoting hydration, strengthening and repairing skin, and firming and conditioning skin.

SUMMARY OF THE INVENTION

The inventors have identified a solution to the problems associated with current cosmetic products. The solution resides in a combination of ingredients including *Rosmari-*

*nus officianalis* leaf extract, *Morus alba* fruit extract, tetrahexyldecyl ascorbate, retinol, *Acmella oleracea* extract, *Alpinia galanga* leaf extract, *Argania spinosa* oil, and/or saccharide isomerate. The combination can be used to create topical compositions that reduce lines and wrinkles, even skin tone, lighten skin tone, increase skin radiance, reduce photodamage, increase elasticity, increase skin barrier function, increase skin firmness, reduce sagging skin, increase anti-oxidant capacity in skin, increase collagen expression in skin, increase elastin expression in skin, increase laminin expression in skin, inhibit MMP-1, inhibit MMP-3, inhibit MMP-9, inhibit pro-inflammatory cytokines (e.g., lipoxygenase, IL-6, Il-8, TNF-α, or VEGF), inhibit elastase expression in skin, and/or increase fibronectin expression in skin. Additional benefits can reduce or mitigate unwanted side effects shown in other retinol products such as erythema or redness in skin, skin dryness, peeling or flaking of skin, and/or skin irritation including without limitation, burning, stinging, itching, or tingling. In some aspects, an effective amount of a combination of *Rosmarinus officianalis* leaf extract, *Morus alba* fruit extract, tetrahexyldecyl ascorbate, retinol, *Acmella oleracea* extract, *Alpinia galanga* leaf extract, *Argania spinosa* oil, and saccharide isomerate was shown in clinical studies to be as effective or more effective than other skin care compositions containing 1 wt. % retinol, even when less than 1 wt. % retinol (e.g., 0.5 wt. % retinol) was used in the combination.

In some aspects, there is disclosed a topical composition that includes any one of, any combination of, or all of *Rosmarinus officianalis* leaf extract, *Morus alba* fruit extract, tetrahexyldecyl ascorbate, retinol, *Acmella oleracea* extract, *Alpinia galanga* leaf extract, *Argania spinosa* oil, and/or saccharide isomerate. The amounts of the ingredients within the composition can vary (e.g., amounts can be as low as 0.000001% to as high as 99% w/w or any range therein). In some aspects, the topical composition includes 0.01 to 10% w/w of *Argania spinosa* oil, 0.01 to 20% w/w of tetrahexyldecyl ascorbate, 0.0001 to 5% w/w of *Acmella oleracea* extract, 0.0001 to 5% w/w of *Alpinia galanga* leaf extract, 0.0001 to 5% w/w of saccharide isomerate, 0.0001 to 2% w/w of *Morus alba* fruit extract, 0.0001 to 2% w/w of *Rosmarinus officinalis* leaf extract, and/or 0.001 to 2% w/w of retinol. In some aspects, the topical composition includes 0.1 to 5% w/w of *Argania spinosa* oil, 0.1 to 10% w/w of tetrahexyldecyl ascorbate, 0.001 to 2% w/w of *Acmella oleracea* extract, 0.001 to 2% w/w of *Alpinia galanga* leaf extract, 0.001 to 2% w/w of saccharide isomerate, 0.001 to 1% w/w of *Morus alba* fruit extract, 0.001 to 1% w/w of *Rosmarinus officinalis* leaf extract, and 0.01 to 1% w/w of retinol. In some instances, the composition contains less than 1% w/w of retinol. In some instances, the composition contains retinol in an amount of 1% w/w, less than 1% w/w, 0.1% w/w to 0.7% w/w, 0.3% w/w to 0.7% w/w, 0.1% w/w to 0.6% w/w, 0.3% w/w to 0.6% w/w, 0.1% w/w to 0.5% w/w, 0.3% w/w to 0.5% w/w, 0.5% w/w to less than 1% w/w, 0.5% w/w to 0.9% w/w, 0.5% w/w to 0.7% w/w, 0.5% w/w to 0.6% w/w, or 0.5% w/w, any amount or range therein.

In some instances, the composition includes an effective amount of *Rosmarinus officinalis* leaf extract, *Morus alba* fruit extract, tetrahexyldecyl ascorbate, retinol, *Acmella oleracea* extract, *Alpinia galanga* leaf extract, *Argania spinosa* oil, and/or saccharide isomerate. In some instances, the composition includes an effective amount of *Rosmarinus officinalis* leaf extract, *Morus alba* fruit extract, tetrahexyldecyl ascorbate, *Acmella oleracea* extract, *Alpinia galanga* leaf extract, *Argania spinosa* oil, saccharide isomerate, and less than 1% w/w retinol, such as 0.5% w/w, to reduce fine lines and/or wrinkles, improve skin color, lighten skin, and/or smooth skin as effective as a larger amount of retinol, such as 1% w/w. In some instances, the composition includes an amount of *Rosmarinus officianalis* leaf extract, *Morus alba* fruit extract, tetrahexyldecyl ascorbate, retinol, *Acmella oleracea* extract, *Alpinia galanga* leaf extract, *Argania spinosa* oil, and/or saccharide isomerate effective to do one or more of the following: reduce lines and wrinkles, even skin tone, lighten skin tone, increase skin radiance, reduce photodamage, increase elasticity, increase skin barrier function, increase skin firmness, reduce sagging skin, increase anti-oxidant capacity (TEAC) in skin, increase collagen expression in skin, increase elastin expression in skin, increase laminin expression in skin, inhibit MMP-1, inhibit MMP-3, inhibit MMP-9, inhibit pro-inflammatory cytokines (e.g., lipoxygenase, IL-6, Il-8, TNF-α, or VEGF), inhibit elastase expression in skin, and/or increase fibronectin expression in skin. In some instances, the composition includes an effective amount of *Rosmarinus officianalis* leaf extract to increase anti-oxidant capacity in skin, inhibit MMP-1, MMP-3, and/or MMP-9 in skin, inhibit pro-inflammatory cytokines lipoxygenase, IL-6, Il-8, TNF-α, and/or VEGF, and/or inhibit elastase expression in skin. In some instances, the composition includes an effective amount of *Morus alba* fruit extract to increase anti-oxidant capacity in skin, increase collagen expression in skin, increase laminin expression in skin, inhibit MMP-1, MMP-3, and/or MMP-9 in skin, inhibit elastase expression in skin, and/or increase fibronectin expression in skin; and/or an effective amount of tetrahexyldecyl ascorbate to increase collagen expression in skin, inhibit MMP-3 and/or MMP-9 in skin, and/or inhibit IL-6; and/or an effective amount of retinol to reduce fine lines and wrinkles by increasing the production of collagen, used to improve skin color by increasing new blood vessels in the skin, and used to fade age spots and soften skin; and/or an effective amount of *Acmella oleracea* extract to increase anti-oxidant capacity in skin, increase collagen expression in skin, increase laminin expression in skin, inhibit MMP-9, and/or inhibit lipoxygenase and/or IL-6; and/or an effective amount of *Alpinia galanga* leaf extract to increase collagen expression in skin, increase elastin expression in skin, and/or increase laminin expression in skin; and/or an effective amount of *Argania spinosa* kernel extract to increase collagen expression in skin, increase elastin expression in skin, increase laminin expression in skin, and/or increase fibronectin expression in skin; and/or an effective amount of Saccharide isomerate to inhibit TNF-α. In some instances, the *Rosmarinus officinalis* leaf extract is an aqueous extract. In some instances, the *Morus alba* fruit extract is an aqueous extract. In some instances, the *Morus alba* fruit extract is a glycerol/water extract. The extraction of the fruits of *Morus alba* can be harvested without the use of alcohol by using a glycerol/water mix as the extraction solvent. In some instances, the *Acmella oleracea* extract is an aqueous extract. In some instances, the *Alpinia galanga* leaf extract is an aqueous extract. In some instances, the *Argania spinosa* kernel extract is an aqueous extract. In some instances, the *Argania spinosa* kernel extract is an oil-based protein hydrosylate extract from oil cakes.

In some instances, the composition further includes water. In some instances, the composition includes 1 to 95% w/w of water. In some instances, the composition further contains one or more of caprylic/capric triglyceride, pentylene glycol, dimethicone, silica, betaine, polysorbate 20, caprylyl glycol, butylene glycol, tocopheryl acetate, butylated hydroxytoluene (BHT), hydroxypropyl cyclodextrin, and/or butylated hydroxyanisole (BHA). In some instances, the composition contains one or more of 0.1 to 10% w/w of caprylic/capric triglyceride, 0.1 to 5% w/w of pentylene glycol, 0.1 to 5% w/w of dimethicone, 0.1 to 5% w/w of silica, 0.01 to 5% w/w of betaine, 0.01 to 5% w/w of polysorbate 20, 0.01 to 1% w/w of carylyl glycol, 0.01 to 1% w/w of butylene glycol, 0.01 to 1% w/w of tocopheryl acetate, 0.01 to 1% w/w of BHT, 0.001 to 0.5% w/w of hydroxypropyl cyclodextrin, and 0.001 to 0.5% w/w of BHA. In some instances, the composition contains 0.1 to 5% w/w of glyceryl stearate and 0.1 to 5% w/w of cetyl alcohol. In some instances, the composition contains one or more of glycerin, ammonium acryloyldimethyltaurate/polyvinylpyrrolidone (VP) copolymer, propanediol, and/or sorbic acid. In some instances, the composition contains 0.1 to 10% w/w of glycerin, 0.1 to 5% w/w of ammonium acryloyldimethyltaurate/VP copolymer, 0.01 to 5% w/w of propanediol, and/or 0.001 to 0.5% w/w of sorbic acid. In some instances, the composition contains *Opuntia tuna* fruit extract. In some instances, the composition contains 0.00001 to 0.001% w/w of *Opuntia tuna* fruit extract.

In some aspects, the compositions of the present invention can further include a surfactant, a silicone containing compounds, a UV agent, an oil, and/or other ingredients identified in this specification or those known in the art. The composition can be a lotion, cream, body butter, mask, scrub, wash, gel, serum, emulsion (e.g., oil-in-water, water-in-oil, silicone-in-water, water-in-silicone, water-in-oil-in-water, oil-in-water-in-oil, oil-in-water-in-silicone, etc.), solutions (e.g., aqueous or hydro-alcoholic solutions), anhydrous bases (e.g., lipstick or a powder), ointments, milk, paste, aerosol, solid forms, eye jellies, gel serums, gel emulsions, etc. The composition can be formulated for topical skin application at least 1, 2, 3, 4, 5, 6, 7, or more times a day during use. In some aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, cps, etc., as measured on a Brookfield Viscometer using a TC spindle at 2.5 rpm at 25° C.).

The compositions, in non-limiting aspects, can have a pH of about 6 to about 9. In some aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include phenoxyethanol, methylparaben, propylparaben, iodopropynyl butylcarbamate, potassium sorbate, sodium benzoate, or any mixture thereof. In some embodiments, the composition is paraben-free.

Compositions of the present invention can have UVA and UVB absorption properties. The compositions can have a sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

The compositions of the present invention can also include any one of, any combination of, or all of the following additional ingredients: a conditioning agent, a moisturizing agent, a pH adjuster, a structuring agent, inorganic salts, a preservative, a thickening agent, a silicone containing compound, an essential oil, a fragrance, a vitamin, a pharmaceutical ingredient, or an antioxidant, or any combination of such ingredients or mixtures of such ingredients. In certain aspects, the composition can include at least two, three, four, five, six, seven, eight, nine, ten, or more, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Methods of use for the compositions disclosed herein are also disclosed. In some aspects, a method is disclosed to reduce lines and wrinkles, even skin tone, lighten skin tone, increase skin radiance, reduce photodamage, increase elasticity, increase skin barrier function, increase skin firmness, reduce sagging skin, or any combination thereof. In some aspects, a method is disclosed to increase anti-oxidant capacity (TEAC) in skin, increase collagen expression in skin, increase elastin expression in skin, increase laminin expression in skin, inhibit MMP-1, inhibit MMP-3, inhibit MMP-9, inhibit pro-inflammatory cytokines (e.g., lipoxygenase, IL-6, Il-8, TNF-α, or VEGF), inhibit elastase expression in skin, and/or increase fibronectin expression in skin, or any combination thereof. In some instances, the method comprises topically applying any one of the compositions disclosed herein to skin in need thereof. In one aspect, any one of the compositions disclosed herein are topically applied and the composition is left on the application area, removed from the application area after a period of time, and/or removed directly after application.

In some aspects, the compositions disclosed herein are used to increase anti-oxidant capacity (TEAC) in skin, which can reduce oxidative damage in skin, can be beneficial for improving skin firmness, reducing sagging skin, and can improve elasticity and reduce signs of ageing. In some aspects, the compositions disclosed herein are used to increase collagen expression in skin, which can be beneficial in reducing the appearance of fine lines or wrinkles and/or reducing the appearance of sagging or non-elastic skin by increasing cross-linking of elastins and collagens, thereby creating a more structurally sound matrix of supportive proteins in the skin. In some aspects, the compositions disclosed herein are used to increase elastin expression in skin, which can be beneficial to help skin resume its shape after stretching and/or contracting. In some aspects, the compositions disclosed herein are used to increase laminin expression in skin, which can be beneficial to the structural integrity of the skin. In some aspects, the compositions disclosed herein are used to inhibit MMP-1, MMP-3, and/or MMP-9, which can slow collagen degradation, reduce fine lines and wrinkles, and can prevent skin darkening and lighten dark spots associated with ageing. In some aspects, the compositions disclosed herein are used to inhibit pro-inflammatory cytokines (e.g., lipoxygenase, IL-6, Il-8, TNF-α, or VEGF), which can be beneficial to inhibit inflammation, decrease redness in skin, lessen uneven pigmentation in skin, and improve structural integrity in skin. In some aspects, the compositions disclosed herein are used to inhibit elastase expression in skin, which can slow the degradation of elastin and can be beneficial to help skin resume its shape after stretching and/or contracting. In some aspects, the compositions disclosed herein are used to increase fibronectin expression in skin, which can be beneficial to the structural integrity of the skin. In some instances, the methods disclosed herein comprise topically applying any one of the composition disclosed herein to skin in need thereof.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse off composition can be a skin cleanser, shampoo, conditioner, or soap. An example of a leave-on composition can be a skin moisturizer, sunscreen, mask, overnight cream, or a day cream.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, mist, dollop, or liquid. The container can include indicia on its surface. The indicia can be a word, an abbreviation, a picture, or a symbol.

It is contemplated that any embodiment discussed in this specification can be implemented with respect to any method or composition of the invention, and vice versa. Furthermore, compositions of the invention can be used to achieve methods of the invention.

In some embodiments, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a serum, a gel, a wash, a body butter, a scrub, a foundation, a night cream, a lipstick, a cleanser, a toner, a sunscreen, a mask, an anti-aging product, a deodorant, an antiperspirant, a perfume, a cologne, etc.

Also disclosed are the following Embodiments 1 to 38 of the present invention. Embodiment 1 is a method for topically treating skin, the method comprising applying to skin a composition comprising a combination of: *Argania spinosa* oil, tetrahexyldecyl ascorbate, *Acmella oleracea* extract, *Alpinia galanga* leaf extract, saccharide isomerate, *Morus alba* fruit extract, *Rosmarinus officinalis* leaf extract, and retinol, wherein topical application of the composition is used to treat skin. Embodiment 2 is the method of Embodiment 1, wherein the composition comprises an effective amount of the combination to provide one or more anti-aging benefits comprising reducing deep lines and wrinkles, evening uneven skin tone, lightening skin tone, increasing skin radiance, reducing photodamage, increasing elasticity of skin, increasing skin firmness, reducing sagging skin, reducing loss of facial volume, and/or increasing skin barrier function. Embodiment 3 is the method of any one of Embodiments 1 to 2, wherein the combination provides one or more anti-aging benefits comprising one or more of inhibiting anti-oxidant capacity in skin, increasing collagen expression in skin, increasing elastin expression in skin, increasing laminin expression in skin, inhibiting MMP-1, inhibiting MMP-3, inhibiting MMP-9, inhibiting pro-inflammatory cytokines (e.g., lipoxygenase, IL-6, Il-8, TNF-α, or VEGF), inhibiting elastase expression in skin, and/or increasing fibronectin expression in skin. Embodiment 4 is the method of any one of Embodiments 1 to 3, wherein the combination reduces or mitigates erythema or redness in skin, skin dryness, peeling or flaking of skin, and/or skin irritation when applied to skin as compared to the same topical composition comprising 1 wt. % retinol and not containing the combination. Embodiment 5 is the method of any one of Embodiments 1 to 4, wherein the composition comprises: 0.1 to 5% by weight of *Argania spinosa* oil, 0.1 to 10% by weight of tetrahexyldecyl ascorbate, 0.001 to 2% by weight of *Acmella oleracea* extract, 0.001 to 2% by weight of *Alpinia galanga* leaf extract, 0.001 to 2% by weight of saccharide isomerate, 0.001 to 1% by weight of *Morus alba* fruit extract, 0.001 to 1% by weight of *Rosmarinus officinalis* leaf extract, and 0.01 to 1% by weight of retinol. Embodiment 6 is the method of any one of Embodiments 1 to 5, the composition further comprising an effective amount of one or more of: water, caprylic/capric triglyceride, pentylene glycol, tetrahexyldecyl ascorbate, dimethicone, silica, betaine polysorbate 20, caprylyl glycol, butylene glycol, tocopheryl acetate, butylated hydroxytoluene (BHT), hydroxypropyl cyclodextrin, and butylated hydroxyanisole (BHA) to moisturize and/or condition skin. Embodiment 7 is the method of any one of Embodiments 1 to 6, the composition further comprising: 1 to 95% by weight water, 0.1 to 10% by weight caprylic/capric triglyceride, 0.1 to 5% by weight pentylene glycol, 0.1 to 5% by weight tetrahexyldecyl ascorbate, 0.1 to 5% by weight dimethicone, 0.1 to 5% by weight silica, 0.01 to 5% by weight betaine, 0.01 to 5% by weight polysorbate 20, 0.01 to 1% by weight caprylyl glycol, 0.01 to 1% by weight butylene glycol, 0.01 to 1% by weight tocopheryl acetate, 0.001 to 1% by weight BHT, 0.001 to 0.5% by weight hydroxypropyl cyclodextrin, and/or 0.001 to 0.5% by weight BHA. Embodiment 8 is the method of any one of Embodiments 1 to 7, the composition further comprising one or more of: glycerin, ammonium acryloyldimethyltaurate, propanediol, sodium phytate, triethanolamine, lactic acid, phenoxyethanol, polyacrylate-13, polyisobutene, sorbic acid, disodium EDTA, alcohol, xanthan gum, and iodopropynyl butylcarbamate. Embodiment 9 is the method of any one of Embodiments 1 to 8, the composition further comprising: 0.1 to 30% by weight glycerin, 0.01 to 10% by weight ammonium acryloyldimethyltaurate, 0.01 to 10% by weight propanediol, 0.01 to 10% by weight sodium phytate, 0.01 to 5% by weight triethanolamine, 0.01 to 5% by weight lactic acid, 0.01 to 5% by weight phenoxyethanol, 0.001 to 2% by weight polyacrylate-13, 0.001 to 1% by weight polyisobutene, 0.0001 to 1% by weight sorbic acid, 0.0001 to 1% by weight disodium EDTA, 0.0001 to 1% by weight alcohol, 0.0001 to 0.5% by weight xanthan gum, and/or 0.0001 to 0.5% by weight iodopropynyl butylcarbamate. Embodiment 10 is the method of any one of Embodiments 1 to 9, wherein the composition is applied to one or more of: a fine line or wrinkle and wherein application of the composition reduces the fine line or wrinkle, skin containing an uneven tone and wherein application of the composition evens skin tone, sagging skin or non-elastic skin and wherein application of the composition increases elasticity in skin, and/or skin with a reduced skin barrier function and wherein application of the composition increases skin barrier function. Embodiment 11 is the method of any one of Embodiments 1 to 10, the composition comprising 40 to 80% by weight of water. Embodiment 12 is the method of any one of Embodiments 1 to 11, the composition comprising 0.1 to 0.7% by weight of retinol. Embodiment 13 is the method of any one of Embodiments 1 to 12, the composition comprising 0.3 to 0.6% by weight of retinol. Embodiment 14 is the method of any one of Embodiments 1 to 13, the composition comprising 0.5% by weight of retinol. Embodiment 15 is the method of any one of Embodiments 1 to 14, wherein *Argania spinosa* oil is an oil extract from the kernel of the Argan tree; *Acmella oleracea* extract is a hydroethanolic flower, leaf, and stem extract; *Alpinia galangal* leaf extract is an aqueous leaf extract; saccharide isomerate extract comprises an exopolysaccharide synthesized by *Vibrio alginolyticus*; *Morus alba* fruit extract is a water and glycerol extract; and/or *Rosmarinus officinalis* leaf extract is a betaine, lactic acid, and water extract. Embodiment 16 is the method of any one of Embodiments 1 to 15, wherein *Acmella oleracea* extract is an extract of dried flower, stem, and/or leaf, the *Morus alba* fruit extract does not comprise an extract of a *Morus alba* seed; and/or *Morus alba* fruit extract is not an ethanolic extract. Embodiment 17 is the method of any one of Embodiments 1 to 16, further comprising: i) applying a facial milk to the skin during or after applying the composition to the skin; and/or 2) combining the facial milk and the composition and applying the combination to the skin, wherein the facial milk comprises squalene, glycerin, *Simmondsia chinensis* (jojoba) seed oil, *Cocos nucifera* (coconut) oil, *Carthamus tinctorius* (safflower) seed oil, and *Olea europaea* (olive) fruit oil. Embodiment 18 is the method of Embodiment 17, wherein the facial milk further comprises water, caprylic/capric triglyceride, glyceryl oleate citrate, hydrogenated lecithin, glycereth-2 cocoate, xanthan gum, disodium EDTA, hydroxypropyl cyclodextrin, benzoic acid, ethylhexylglycerin, phenoxyethanol, and iodopropynyl butylcarbamate. Embodiment 19 is the method of Embodiment 17, further comprising mixing the composition and the facial milk to create a mixture, and applying the mixture to skin. Embodiment 20 is the method of any one of Embodiments 1 to 19, wherein the composition further comprises squalene, glycerin, *Simmondsia chinensis* (jojoba) seed oil, *Cocos nucifera* (coconut) oil, *Carthamus tinctorius* (safflower) seed oil, and *Olea europaea* (olive) fruit oil, water, caprylic/capric triglyceride, glyceryl oleate citrate, hydrogenated lecithin, glycereth-2 cocoate, xanthan gum, disodium EDTA, hydroxypropyl cyclodextrin, benzoic acid, ethylhexylglycerin, phenoxyethanol, and iodopropynyl butylcarbamate. Embodiment 21 is a topical skin composition comprising a combination of: *Argania spinosa* oil, tetrahexyldecyl ascorbate, *Acmella oleracea* extract, *Alpinia galanga* leaf extract, saccharide isomerate, *Morus alba* fruit extract, *Rosmarinus officinalis* leaf extract, and retinol. Embodiment 22 is the topical skin composition of Embodiment 21, comprising an effective amount of the combination to provide one or more anti-aging benefits comprising reducing deep lines and wrinkles, evening uneven skin tone, lightening skin tone, increasing skin radiance, reducing photodamage, increasing elasticity of skin, increasing skin firmness, reducing sagging skin, reducing loss of facial volume, and/or increasing skin barrier function. Embodiment 23 is the topical skin composition of any one of Embodiments 21 to 22, wherein the combination provides anti-aging benefits comprising one or more of inhibiting anti-oxidant capacity in skin, increasing collagen expression in skin, increasing elastin expression in skin, increasing laminin expression in skin, inhibiting MMP-1, inhibiting MMP-3, inhibiting MMP-9, inhibiting pro-inflammatory cytokines (e.g., lipoxygenase, IL-6, Il-8, TNF-α, or VEGF), inhibiting elastase expression in skin, and/or increasing fibronectin expression in skin. Embodiment 24 is the topical skin composition of any one of Embodiments 21 to 23, wherein the combination reduces or mitigates erythema or redness in skin, skin dryness, peeling or flaking of skin, and/or skin irritation when applied to skin as compared to the same topical composition comprising 1 wt. % retinol and not containing the combination. Embodiment 25 is the topical skin composition of any one of Embodiments 21 to 24, comprising: 0.1 to 5% by weight of *Argania spinosa* oil, 0.1 to 10% by weight of tetrahexyldecyl ascorbate, 0.001 to 2% by weight of *Acmella oleracea* extract, 0.001 to 2% by weight of *Alpinia galanga* leaf extract, 0.001 to 2% by weight of saccharide isomerate, 0.001 to 1% by weight of *Morus alba* fruit extract, 0.001 to 1% by weight of *Rosmarinus officinalis* leaf extract, and 0.01 to 1% by weight of retinol. Embodiment 26 is the topical skin composition of any one of Embodiments 21 to 25, wherein the composition is formulated as a serum, cream, or cleanser. Embodiment 27 is the topical skin composition of any one of Embodiments 21 to 26, further comprising an effective amount of: water, caprylic/capric triglyceride, pentylene glycol, tetrahexyldecyl ascorbate, dimethicone, silica, betaine, polysorbate 20, caprylyl glycol, butylene glycol, tocopheryl acetate, BHT, hydroxypropyl cyclodextrin, and BHA to moisturize and/or condition skin. Embodiment 28 is the topical skin composition of any one of Embodiments 21 to 27, further comprising: 1 to 95% by weight water, 0.1 to 10% by weight caprylic/capric triglyceride, 0.1 to 5% by weight pentylene glycol, 0.1 to 5% by weight tetrahexyldecyl ascorbate, 0.1 to 5% by weight dimethicone, 0.1 to 5% by weight silica, 0.01 to 5% by weight betaine, 0.01 to 5% by weight polysorbate 20, 0.01 to 1% by weight caprylyl glycol, 0.01 to 1% by weight butylene glycol, 0.01 to 1% by weight tocopheryl acetate, 0.01 to 1% by weight BHT, 0.001 to 0.5% by weight hydroxypropyl cyclodextrin, and/or 0.001 to 0.5% by weight BHA. Embodiment 29 is the topical skin composition of any one of Embodiments 21 to 28, further comprising: glycerin, ammonium acryloyldimethyltaurate, propanediol, sodium phytate, triethanolamine, lactic acid, phenoxyethanol, polyacrylate-13, polyisobutene, sorbic acid, disodium EDTA, alcohol, xanthan gum, and iodopropynyl butylcarbamate. Embodiment 30 is the topical skin composition of any one of Embodiments 21 to 29, further comprising: 0.1 to 30% by weight glycerin, 0.01 to 10% by weight ammonium acryloyldimethyltaurate, 0.01 to 10% by weight propanediol, 0.01 to 10% by weight sodium phytate, 0.01 to 5% by weight triethanolamine, 0.01 to 5% by weight lactic acid, 0.01 to 5% by weight phenoxyethanol, 0.001 to 2% by weight polyacrylate-13, 0.001 to 1% by weight polyisobutene, 0.0001 to 1% by weight sorbic acid, 0.0001 to 1% by weight disodium EDTA, 0.0001 to 1% by weight alcohol, 0.0001 to 0.5% by weight xanthan gum, and/or 0.0001 to 0.5% by weight iodopropynyl butylcarbamate. Embodiment 31 is the topical skin composition of any one of Embodiments 21 to 30, comprising 0 to 90% by weight of water. Embodiment 32 is the topical skin composition of any one of Embodiments 21 to 31, comprising 0.1 to 0.7% by weight of retinol. Embodiment 33 is the topical skin composition of any one of Embodiments 21 to 32, comprising 0.3 to 0.6% by weight of retinol. Embodiment 34 is the topical skin composition of any one of Embodiments 21 to 33, comprising 0.5% by weight of retinol. Embodiment 35 is the topical skin composition of any one of Embodiments 21 to 34, wherein *Argania spinosa* oil is an oil extract from the kernel of the Argan tree; *Acmella oleracea* extract is a hydroethanolic flower, leaf, and stem extract; *Alpinia galangal* leaf extract is an aqueous leaf extract; saccharide isomerate extract comprises an exopolysaccharide synthesized by *Vibrio alginolyticus*; *Morus alba* fruit extract is a water and glycerol extract; and/or *Rosmarinus officinalis* leaf extract is a betaine, lactic acid, and water extract. Embodiment 36 is the topical skin composition of any one of Embodiments 21 to 35, further comprising 0.001 to 2% by weight of *Opuntia tuna* (prickly pear) extract. Embodiment 37 is the topical skin composition of any one of Embodiments 21 to 36, further comprising squalene, glycerin, *Simmondsia chinensis* (jojoba) seed oil, *Cocos nucifera* (coconut) oil, *Carthamus tinctorius* (safflower) seed oil, and *Olea europaea* (olive) fruit oil. Embodiment 38 is the topical skin composition of Embodiment 37, further comprising water, caprylic/capric triglyceride, glyceryl oleate citrate, hydrogenated lecithin, glycereth-2 cocoate, xanthan gum, disodium EDTA, hydroxypropyl cyclodextrin, benzoic acid, ethylhexylglycerin, phenoxyethanol, and iodopropynyl butylcarbamate.

"Topical application" means to apply or spread a composition onto the surface of lips or keratinous tissue. "Topical skin composition" includes compositions suitable for topical application on skin and/or keratinous tissue. Such compositions are typically dermatologically-acceptable in that they do not have undue toxicity, incompatibility, instability, allergic response, and the like, when applied to skin and/or keratinous tissue. Topical skin care compositions of the present invention can have a selected viscosity to avoid significant dripping or pooling after application to skin and/or keratinous tissue.

"Keratinous tissue" includes keratin-containing layers disposed as the outermost protective covering of mammals and includes, but is not limited to, lips, skin, hair, and nails.

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase, such as a measurable increase of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the terms "comprising," "including," "having," or "containing," or any variations of these terms, in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the phrase "consisting essentially of," a basic and novel property of the compositions and methods of the present invention is the ability to reduce the appearance of fine lines and wrinkles, moisturize skin, promote hydration, strengthen and repair skin, firm and condition skin, improve skin barrier function, reduce skin desquamation, reduce skin roughness, and increase skin lubricity.

Other objects, features, and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
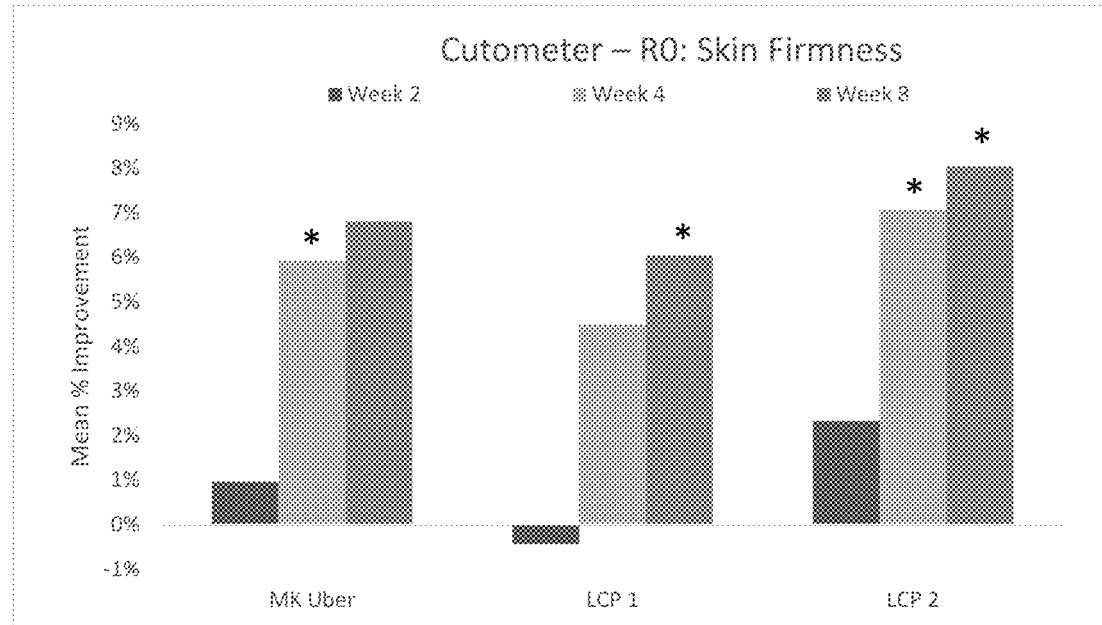
FIG. 1 shows results for skin firmness using a cutometer as a measurement tool. Data indicated by an * is statistically significant compared to Baseline values.

As noted above, the present invention provides a solution to the problems associated with current cosmetic products. In some embodiments, an effective amount of a combination of *Rosmarinus officianalis* leaf extract, *Morus alba* fruit extract, tetrahexyldecyl ascorbate, retinol, *Acmella oleracea* extract, *Alpinia galanga* leaf extract, *Argania spinose* oil, and saccharide isomerate was shown in clinical studies to reduce lines and wrinkles, even skin tone, lighten skin tone, increase skin radiance, reduce photodamage, increase elasticity, increase skin barrier function, increase skin firmness, reduce sagging skin, as well as, or better than, some other skin care compositions containing 1 wt. % retinol, even when less than 1 wt. % retinol (e.g., 0.5 wt. % retinol) was used in the combination. The combination of ingredients was also shown to increase anti-oxidant capacity (TEAC) in skin, increase collagen expression in skin, increase elastin expression in skin, increase laminin expression in skin, inhibit MMP-1, inhibit MMP-3, inhibit MMP-9, inhibit pro-inflammatory cytokines (e.g., lipoxygenase, IL-6, Il-8, TNF-α, or VEGF), inhibit elastase expression in skin, and/or increase fibronectin expression in skin.

*Rosmarinus officianalis* leaf extract was shown to increase anti-oxidant capacity by 52% in skin, inhibit MMP-1 by 98%, MMP-3 by 40%, and MMP-9 by 61% in skin, inhibit pro-inflammatory cytokines lipoxygenase by 54%, IL-6 by 83%, Il-8 by 98%, TNF-α by 85%, and VEGF by 50%, and inhibit elastase expression by 54% in skin. *Morus alba* fruit extract was shown to increase anti-oxidant capacity by 98% in skin, increase collagen expression by 27% in skin, increase laminin expression by 14% in skin, inhibit MMP-1 by 96%, MMP-3 by 29%, and MMP-9 by 84% in skin, inhibit elastase expression by 25% in skin, and increase fibronectin expression by 13% in skin. Tetrahexyldecyl ascorbate was shown to increase collagen expression by 50% in skin, inhibit MMP-3 by 38% and MMP-9 by 11% in skin, and inhibit TL-6 by 38%. *Acmella oleracea* extract was shown to increase anti-oxidant capacity by 80% in skin, increase collagen expression by 41% in skin, increase laminin expression by 39% in skin, inhibit MMP-9 by 80%, and inhibit lipoxygenase by 98% and TL-6 by 80%. *Alpinia galanga* leaf extract was shown to increase collagen expression by 25% in skin, increase elastin expression by 43% in skin, and increase laminin expression by 500% in skin. *Argania spinosa* kernel extract was shown to increase collagen expression by 28% in skin, increase elastin expression by 82% in skin, increase laminin expression by 135% in skin, and increase fibronectin expression by 22% in skin. Saccharide isomerate was shown to inhibit TNF-α by 88%.

A particular composition of the present invention is designed to work as a topical composition. The composition relies on a unique combination of any one of, any combination of, or all of *Rosmarinus officianalis* leaf extract, *Morus alba* fruit extract, tetrahexyldecyl ascorbate, retinol, *Acmella oleracea* extract, *Alpinia galanga* leaf extract, *Argania spinosa* oil, and/or saccharide isomerate. These combinations can be used to create topical compositions that reduce lines and wrinkles, even skin tone, lighten skin tone, increase skin radiance, reduce photodamage, increase elasticity, increase skin barrier function, increase skin firmness, reduce sagging skin, increase anti-oxidant capacity (TEAC) in skin, increase collagen expression in skin, increase elastin expression in skin, increase laminin expression in skin, inhibit MMP-1, inhibit MMP-3, inhibit MMP-9, inhibit pro-inflammatory cytokines (e.g., lipoxygenase, IL-6, Il-8, TNF-α, or VEGF), inhibit elastase expression in skin, and/or increase fibronectin expression in skin. Non-limiting examples of such compositions are provided in Table 1 of Example 1 and Table 3 of Example 4 below.

A particular composition of the present invention is designed to work as a topical composition. The composition relies on a unique combination of any one of, any combination of, or all of water, caprylic/capric triglyceride, glycerin, pentylene glycol, tetrahexyldecyl ascorbate, ammonium acryloyldimethyltaurate/VP copolymer, dimethicone, *Argania spinosa* kernel oil, propanediol, glyceryl oleate citrate, sodium phytate, triethanolamine, silica, retinol, *Acmella oleracea* extract, *Alpinia galanga* leaf extract, *Rosmarinus officianalis* leaf extract, *Morus alba* fruit extract, lactic acid, betaine, tocopheryl acetate, saccharide isomerate, polysorbate-20, polyacrylate-13, butylene glycol, polyisobutene, hydroxypropyl cyclodextrin, sorbic acid, alcohol, disodium EDTA, xanthan gum, caprylyl glycol, phenoxyethanol, iodopropynyl butylcarbamate, BHT, and BHA. These combinations can be used to create topical compositions that reduce lines and wrinkles, even skin tone, lighten skin tone, increase skin radiance, reduce photodamage, increase elasticity, increase skin barrier function, increase skin firmness, reduce sagging skin, increase anti-oxidant capacity (TEAC) in skin, increase collagen expression in skin, increase elastin expression in skin, increase laminin expression in skin, inhibit MMP-1, inhibit MMP-3, inhibit MMP-9, inhibit pro-inflammatory cytokines (e.g., lipoxygenase, IL-6, Il-8, TNF-α, or VEGF), inhibit elastase expression in skin, and/or increase fibronectin expression in skin. Non-limiting examples of such compositions are provided in Table 1 of Example 1 and Table 3 of Example 4 below.

A particular composition of the present invention is designed to work as a facial milk. The composition relies on a unique combination of any one of, any combination of, or all of water, squalene, caprylic/capric triglyceride, glycerin, glyceryl oleate citrate, *Simmondsia chinensis* (jojoba) seed oil, *Cocos nucifera* (coconut) oil, *Carthamus tinctorius* (safflower) seed oil, *Olea europaea* (olive) fruit oil, hydrogenated lecithin, glycereth-2 cocoate, xanthan gum, disodium EDTA, hydroxypropyl cyclodextrin, benzoic acid, ethylhexylglycerin, phenoxyethanol, and iodopropynyl butylcarbamate. These combinations can be used to create facial milk formulations that calm, soothe, and moisturize skin. Particularly, the *Simmondsia chinensis* (jojoba) seed oil, *Cocos nucifera* (coconut) oil, *Carthamus tinctorius* (safflower) seed oil, *Olea europaea* (olive) fruit oil, and squalene calm and soothe skin while providing immediate moisture to skin. These components have also surprisingly been found to reduce the effects of retinol to irritate skin while maintaining the positive effects of retinol. In some instances, formulations containing these ingredients can be applied to skin before, after, or at the same time that a composition containing retinol is applied. Non-limiting examples of such compositions are provided in Table 1 of Example 1 and Table 4 of Example 4 below.

In some instances, a topical composition as disclosed herein and a facial milk as disclosed herein can be used to provide one or more anti-aging benefits to skin. According to some implementations, a topical skin composition as disclosed herein and a facial milk as disclosed herein can be used in combination either by mixing or application at the same time, or application of the topical skin composition followed by the facial milk. A small amount of a topical composition comprising any one of, any combination of, or all of *Rosmarinus officianalis* leaf extract, *Morus alba* fruit extract, tetrahexyldecyl ascorbate, retinol, *Acmella oleracea* extract, *Alpinia galanga* leaf extract, *Argania spinosa* oil, and/or saccharide isomerate can be combined with a small amount of a facial milk comprising glycerin, *Simmondsia chinensis* (jojoba) seed oil, *Cocos nucifera* (coconut) oil, *Carthamus tinctorius* (safflower) seed oil, *Olea europaea* (olive) fruit oil, and squalene. In some implementations, the mixture can be applied to the forehead, cheeks, nose, and chin in an upward, outward motion, avoiding the eye area. In some implementations, the topical composition and the facial milk are mixed before application. In yet other implementations, the topical composition and the facial milk are not mixed but are applied to the skin at the same time. In some implementations, a small amount of a topical composition comprising any one of, any combination of, or all of *Rosmarinus officianalis* leaf extract, *Morus alba* fruit extract, tetrahexyldecyl ascorbate, retinol, *Acmella oleracea* extract, *Alpinia galanga* leaf extract, *Argania spinosa* oil, and/or saccharide isomerate can be applied to the forehead, cheeks, nose, and chin and then smoothed on the entire face in an upward, outward motion, avoiding the eye area. Then, a small amount of a facial milk comprising glycerin, *Simmondsia chinensis* (jojoba) seed oil, *Cocos nucifera* (coconut) oil, *Carthamus tinctorius* (safflower) seed oil, *Olea europaea* (olive) fruit oil, and squalene can be applied to the forehead, cheeks, nose, and chin and then smoothed on the entire face in an upward, outward motion, avoiding the eye area. In some preferred implementations, sunscreen can be used on the treated skin.

Some compositions disclosed herein can be applied to the skin and remain on the skin for a period of time (e.g., at least 1, 2, 3, 4, 5, 10, 20, 30, or 60 minutes or more). After which, the composition, if needed, can be rinsed from the skin or peeled from the skin. Some compositions disclosed herein can be applied to the skin and immediately rinsed from the skin. Some compositions disclosed herein can be applied to the skin and absorbed at least in part by the skin.

These and other non-limiting aspects of the present invention are described in the following sections.

A. Active Ingredients

*Rosmarinus officinalis* leaf extract is an extract from the leaf of *Rosmarinus officinalis*. *Rosmarinus officinalis* is native to the Mediterranean region, and is a woody, perennial herb with fragrant, evergreen, needle-like leaves and white, pink, purple, or blue flowers. It is a shrub that can reach up to 1.5 meters in height with leaves that are about 2 to 4 cm long with green (top surface) and white (bottom surface) coloring. In some aspects, the *Rosmarinus officinalis* leaf extract can be obtained from the leaf of *Rosmarinus officinalis*. The leaf can be subjected to an eutectigenesis extraction process using a fluid extraction mixture comprising betaine or hydrated betaine, a hydrogen bond donor compound (e.g., polyols, organic acids, etc.), and water. In some instances, the leaf portion can be crushed or macerated and then subjected to the aforementioned eutectic fluid extraction mixture to obtain a eutectic extract. The eutectic extract can then be used in the compositions of the present invention. In some instances, the hydrogen bond donor is an organic acid, preferably lactic acid. Eutectigenesis utilizes eutectic solvents which are mixtures of compounds having melting points lower than those of their constituents taken in isolation. In some instances, *Rosmarinus officinalis* is commercially available. In some instances, *Rosmarinus officinalis* can be supplied by Naturex (France) under the trade name ROSEMARY EUTECTYS™. It has been determined that an effective amount of *Rosmarinus officianalis* leaf extract can be used to increase anti-oxidant capacity in skin, inhibit MMP-1, MMP-3, and/or MMP-9 in skin, inhibit pro-inflammatory cytokines lipoxygenase, IL-6, Il-8, TNF-α, and/or VEGF, and/or inhibit elastase expression in skin.

*Morus alba* fruit extract is an extract of white mulberry fruit, a tree native to northern China. In some instances, *Morus alba* fruit extract is commercially available from Naturex, which supplies *Morus alba* fruit extract under the trade name DERMOFEEL® ENLIGHT. In some instances, the extract is a glycerol/water extract. In some instances, the extraction of the fruits of *Morus alba* can be harvested under organic conditions without the use of alcohol by using an organic glycerol/water mix as the extraction solvent. It has been determined that this ingredient can be used to increase anti-oxidant capacity in skin, increase collagen expression in skin, increase laminin expression in skin, inhibit MMP-1, MMP-3, and/or MMP-9 in skin, inhibit elastase expression in skin, and/or increase fibronectin expression in skin.

Tetrahexyldecyl ascorbate, also known as ascorbyl tetraisopalmitate, is a vitamin C derivative that functions as an antioxidant and skin conditioner agent. In some instances, tetrahexyldecyl ascorbate is commercially available from Barnet, which supplies tetrahexyldecyl ascorbate under the trade name BV-OSC™. It has been determined that this ingredient can be used to increase collagen expression in skin, inhibit MMP-3 and/or MMP-9 in skin, and/or inhibit IL-6.

Retinol, also known as Vitamin $A_1$, plays an essential role in the health of skin and mucous membranes. It can be used for treatment of acne and keratosis pilaris in topical compositions. It has been determined that an effective amount of retinol can be used to reduce and/or fade dark spots in skin, reduce skin discoloration, and/or reduce fine lines and wrinkles.

*Acmella oleracea* extract is an extract from the *Acmella oleracea* plant. *Acmella oleracea* can be found in South America, Madagascar, and the Mascarene Islands. In some aspects, the *Acmella oleracea* extract is from the combination of the flower, leaf, and stem portions of *Acmella oleracea*. These portions can be combined and then crushed or macerated or crushed or macerated and then combined. The resulting crushed or macerated flower/leaf/stem material can then be subjected to a hydro-alcoholic (preferably hydro-ethanolic) extraction process or a hydro-alcohol-polyol extraction process. The polyol in some instances can be 1,3-propanediol. The alcohol can be removed from the resulting extract. The *Acmella oleracea* extract can be then be used in the compositions of the present invention. In some instances, the *Acmella oleracea* flower/leaf/stem extract can be obtained from a hydro-ethanol-1,3-propanediol solvent mixture. The resulting extract can then be used in the compositions of the present invention or can be further processed to remove the ethanol and can then be used in the compositions of the present invention. Alternatively, the extracting solvent can be a combination of water and polyol, preferably 1,3-propanediol, without an alcohol. The amounts of water, alcohol, and/or polyol present in the reaction mixture can be modified as desired. In some instances, *Acmella oleracea* extract is commercially available. In some instances, *Acmella oleracea* extract can be supplied by Gattefossé (France) under the trade name GATULINE® EXPRESSION AF. It has been determined that an effective amount of *Acmella oleracea* extract can be used to increase anti-oxidant capacity in skin, increase collagen expression in skin, increase laminin expression in skin, inhibit MMP-9, and/or inhibit lipoxygenase and/or IL-6.

*Alpinia galanga* leaf extract is from the leaf of *Alpinia galangal*, also known as "galangal," "greater galangal," "Java galangal," or "Siamese ginger." In some instances, *Alpinia galanga* leaf extract is an aqueous extract. In some instances, this ingredient is commercially available from BASF Care Creations, which supplies *Alpinia galanga* leaf extract under the trade name Hyalufix™. It has been determined that an effective amount of *Alpinia galanga* leaf extract can be used to increase collagen expression in skin, increase elastin expression in skin, and/or increase laminin expression in skin.

*Argania spinosa* kernel extract is an extraction from the kernel of the Argan tree, which is native to the Mediterranean region. In some instances, *Argania spinosa* kernel extract is commercially available from BASF, which supplies *Argania spinosa* kernel extract under the trade name Lipofructyl Argan BHT™. The extract is an oil-based protein hydrosylate extract from oil cakes. It has been determined that this ingredient can be used to increase collagen expression in skin, increase elastin expression in skin, increase laminin expression in skin, and/or increase fibronectin expression in skin.

Saccharide isomerate is an exopolysaccharide, which can be synthesized by a microorganism called *Vibrio alginolyticus*, belonging to the family of Thalasso plankton. In some instances, this ingredient is commercially available from Barnet products, which supplies saccharide isomerate under the trade name Benoiderm™. In some instances, this ingredient is commercially available under the trade name Benoitine™, also supplied by Barnet products. It has been determined that an effective amount of saccharide isomerate can be used to inhibit TNF-α.

This combination of ingredients can be used in different product forms to treat various skin conditions. By way of non-limiting examples, the combination of ingredients can be formulated in an emulsion (e.g., oil in water, water in oil), a gel, a serum, a gel emulsion, a gel serum, a lotion, a mask, a scrub, a wash, a cream, or a body butter.

The extracts described herein can be extracts made through extraction methods known in the art and combinations thereof. Non-limiting examples of extraction methods include the use of liquid-liquid extraction, solid phase extraction, aqueous extraction, ethyl acetate, alcohol, acetone, oil, supercritical carbon dioxide, heat, pressure, pressure drop extraction, ultrasonic extraction, etc. Extracts can be a liquid, solid, dried liquid, re-suspended solid, etc.

B. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.70%, 6.8%, 6.9%, 7.0%, 7.1%, 7.2%, 7.3% 7.4% 7.5% 7.6%, 7.7% 7.8%, 7.9% 8.0%, 8.1%, 8.2%, 8.3%, 8.4%, 8.5%, 8.6%, 8.7%, 8.8%, 8.9%, 9.0%, 9.1%, 9.2%, 9.3% 9.4% 9.5% 9.6%, 9.7% 9.8%, 9.9% 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

C. Vehicles

The compositions of the present invention can include or be incorporated into all types of vehicles and carriers. The vehicle or carrier can be a pharmaceutically or dermatologically acceptable vehicle or carrier. Non-limiting examples of vehicles or carriers include water, glycerin, alcohol, oil, a silicon containing compound, a silicone compound, and wax. Variations and other appropriate vehicles will be apparent to the skilled artisan and are appropriate for use in the present invention. In certain aspects, the concentrations and combinations of the compounds, ingredients, and agents can be selected in such a way that the combinations are chemically compatible and do not form complexes which precipitate from the finished product.

D. Structure

The compositions of the present invention can be structured or formulated into a variety of different forms. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, masks, scrubs, body butters, peels, and ointments. Variations and other structures will be apparent to the skilled artisan and are appropriate for use in the present invention.

E. Additional Ingredients

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrance agents (artificial and natural; e.g., gluconic acid, phenoxyethanol, and triethanolamine), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), flavoring agents/aroma agents (e.g., *Stevia rebaudiana* (sweetleaf) extract, and menthol), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as para-aminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., *Aloe vera*, chamomile, cucumber extract, *Ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, saccharide isomerate, and mannitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, biosaccharide gum-1, ethylhexylglycerin, pentylene glycol, hydrogenated polydecene, octyldodecyl oleate, gluconolactone, calcium gluconate, cyclohexasiloxane, and dipotassium glycyrrhizate). Non-limiting examples of some of these ingredients are provided in the following subsections.

a. UV Absorption and/or Reflecting Agents

UV absorption and/or reflecting agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate (octinoxate), isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, saccharide isomerate, sodium glucuronate, sodium PCA, sorbitol, sucrose, trehalose, urea, and xylitol.

Other examples include acetylated lanolin, acetylated lanolin alcohol, alanine, algae extract, *Aloe barbadensis*, *Aloe barbadensis* extract, *Aloe barbadensis* gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamom (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, *Geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, maltitol, matricaria (*Chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, plankton extract, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include sodium cocoyl glutamate, hydroxypropyl cyclodextrin, stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (see U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, cyclohexasiloxane, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e., normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e., dimethicones having a viscosity of about 50 cst or less (e.g., dimethicones such as Dow Corning 200-0.5 cst Fluid). The Dow Corning Fluids are available from Dow Corning Corporation, Midland, Michigan. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Michigan.

g. Exfoliating Agent

Exfoliating agents include ingredients that remove dead skin cells on the skin's outer surface. These agents may act through mechanical, chemical, and/or other means. Non-limiting examples of mechanical exfoliating agents include abrasives such as pumice, silica, cloth, paper, shells, beads, solid crystals, solid polymers, etc. Non-limiting examples of chemical exfoliating agents include acids and enzyme exfoliants. Acids that can be used as exfoliating agents include, but are not limited to, glycolic acid, lactic acid, citric acid, a hydroxy acids, beta hydroxy acids, etc. Other exfoliating agents known to those of skill in the art are also contemplated as being useful within the context of the present invention.

h. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 1600 to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

i. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyltaurate/VP copolymer, or a mixture of them.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., CARBOPOL™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835, 206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

j. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

F. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

A. Example 1 (Materials Used)

The active ingredients in Table 1 were used to obtain the in vitro data noted below.

TABLE 1

| Ingredient |
| --- |
| *Rosmarinus officianalis* leaf extract, supplied by Naturex (France) under the trade name ROSEMARY EUTECTYS ™. |
| *Morus alba* fruit extract, supplied by Naturex under the trade name DERMOFEEL ® ENLIGHT. |
| Tetrahexyldecyl ascorbate, supplied by Barnet under the trade name BV-OSC ™. |

TABLE 1-continued

Ingredient

Retinol, supplied by BASF under the trade name Retinol 50 C.
Acmella oleracea extract, supplied by Gattefossé (France) under the trade name GATULINE ® EXPRESSION AF.
Alpinia galanga leaf extract, supplied by BASF Care Creations under the trade name Hyalufix ™.
Argania spinosa kernel extract, supplied by BASF, under the trade name Lipofructyl Argan BHT ™.
Saccharide Isomerate, supplied by Barnet under the trade name Benoitine ™.

B. Example 2 (Clinical Efficacy Study)

It has been unexpectedly determined that use of a combination of *Rosmarinus officianalis* leaf extract, *Morus alba* fruit extract, tetrahexyldecyl ascorbate, *Acmella oleracea* extract, *Alpinia galanga* leaf extract, *Argania spinosa* oil, saccharide isomerate, and less than 1 wt. % retinol (e.g., 0.5 wt. % as tested in this clinical study), is as effective as, or more effective than other formulations containing 1% retinol in all clinical tests such as skin lightness and skin redness as measured by chromameter, skin firmness and elasticity as measured by a cutometer, reduction in wrinkles and mottled pigmentation as scored by a dermatologist, increase in skin radiance, skin firmness, and elasticity as scored by a dermatologist, reduction in sagging skin and overall photodamage as scored by a dermatologist, increase in smoothness and skin tone evenness as scored by a dermatologist, and mild or no erythema, redness, dryness, peeling, flaking, irritation, burning, stinging, itching, or tingling as self-scored by the clinical study participants. These results demonstrate that the benefits of use of 1 wt. % retinol can be obtained by the combination of ingredients containing less than 1 wt. % retinol while also reducing some of the unwanted effects of using higher concentrations of retinol (e.g., increased skin irritation, skin dryness, sunlight sensitivity, burning, stinging, itching, and tingling sensation in skin caused by 1 wt. % retinol). This data suggests that the combination of ingredients may act synergistically with retinol or that a combination of *Rosmarinus officianalis* leaf extract, *Morus alba* fruit extract, tetrahexyldecyl ascorbate, *Acmella oleracea* extract, *Alpinia galanga* leaf extract, *Argania spinosa* oil, saccharide isomerate can be an effective substitute for retinol or a portion of retinol, while avoiding unwanted side effects.

A randomized, controlled, double-blind clinical study was performed to evaluate the tolerability and efficacy of three facial emulsion treatment products to improve photo-damaged skin, including a product following the present invention and two of the leading competitor retinol products. The study took place over the course of nine (9) weeks, wherein the first week was a "wash-out" to ensure previous product usage by participants does not affect this study and the next eight weeks included test product usage. The test emulsion products used by participants were either the formulation of Table 3 containing 0.5% retinol ("MK Uber") (26 participants), or Leading Competitor Product 1 containing 1% retinol ("LCP 1") (27 participants), or Leading Competitor Product 2 containing 1% retinol ("LCP 2") (27 participants). Supplemental products used by all participants in the study included Mary Kay® Botanical Effects® Cleanse Formula 1 for dry skin (facial cleanser), Mary Kay® Intense Moisturizing Cream 0.5% Retinol for dry skin (night cream), and Neutrogena® Ultra Sheer® Dry-Touch Sunscreen Lotion SPF 30 (day cream SPF 30). Evaluation of photo-damaged skin was performed at the Baseline, Week 2, Week 4, and Week 8 of treatment. Methods for evaluation included a board-certified dermatologist evaluation for tolerance, expert clinical evaluation for efficacy, cutometer for skin firmness and elasticity, chromameter for lightness, and VISIA images to review photo-damage in skin. The results are charted in FIGS. 1 to 12. Statistically significant results are labeled with an asterisk (*).

Participants were healthy female volunteers, aged 35 to 70 years, with a maximum of two participants aged 66 to 70 per treatment group. Participants had Fitzpatrick skin types I to III (I—Always burns easily, never tans; II—Always burns easily, tans minimally; and III—Burns moderately, tans gradually), and were regular users of facial cleansing and moisturizing products in their skin care routine. Participants were also tested at Screening and Baseline visits and scored moderate severity, or 4 to 6 on a 0 to 9 scale, for coarse wrinkles in the forehead area and facial pigmentation.

Figure 2:
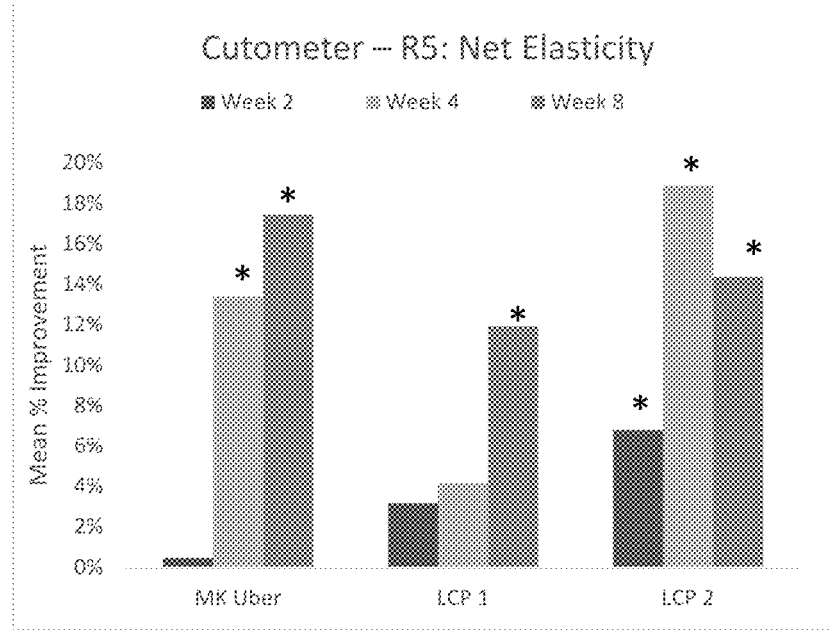
FIG. 2 shows results for net elasticity of skin using a cutometer as a measurement tool. Data indicated by an * is statistically significant compared to Baseline values.

Participants were instructed to perform a morning routine and an evening routine using the test products. The morning routine included applying facial cleanser and then applying the day cream SPF 30 to the entire face and forehead each morning for the duration of the study. The evening routine included (1) applying the facial cleanser, (2) applying a "pea-sized" amount of the test facial emulsion product to the forehead, nose, cheeks, and chin, and (3) applying a "pea-sized" amount of the night cream to the forehead, nose, cheeks, and chin. For Weeks 0 to 2, participants were instructed to apply the test facial emulsion every other day in the evening during the evening routine. For Weeks 3 to 8, participants were instructed to apply the test facial emulsion once a day in the evening during the evening routine. Skin firmness, shown in FIG. 1, and net elasticity, shown in FIG. 2, were measured using a cutometer at the end of Week 2, Week 4, and Week 8, which were compared to Baseline measurements. FIGS. 1 and 2 show the average percentage improvement over baseline for each test product. For skin firmness, MK Uber and LCP 2 showed significant improvement in Week 4 and Week 8. LCP 1 showed significant improvement in Week 8. For net elasticity, MK Uber showed statistically significant improvement in Week 4 and Week 8. LCP 2 showed statistically significant improvement in Week 2, Week 4, and Week 8. LCP1 showed statistically significant improvement in Week 8.

Figure 3:
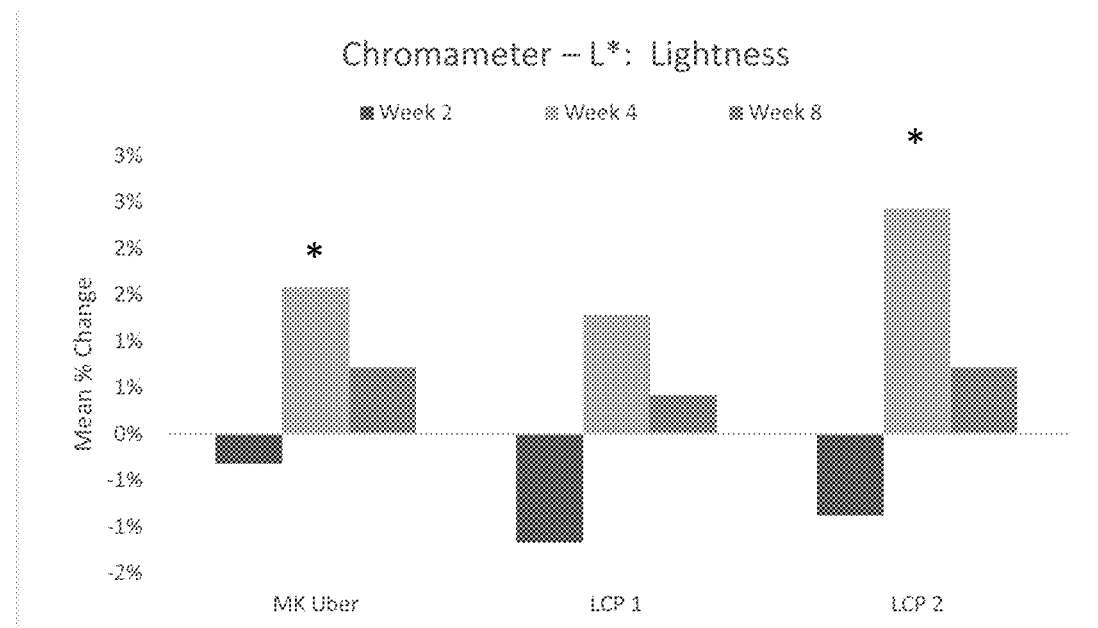
FIG. 3 shows results for lightness of skin using a chromameter as a measurement tool. Data indicated by an * is statistically significant compared to Baseline values.
Figure 4:
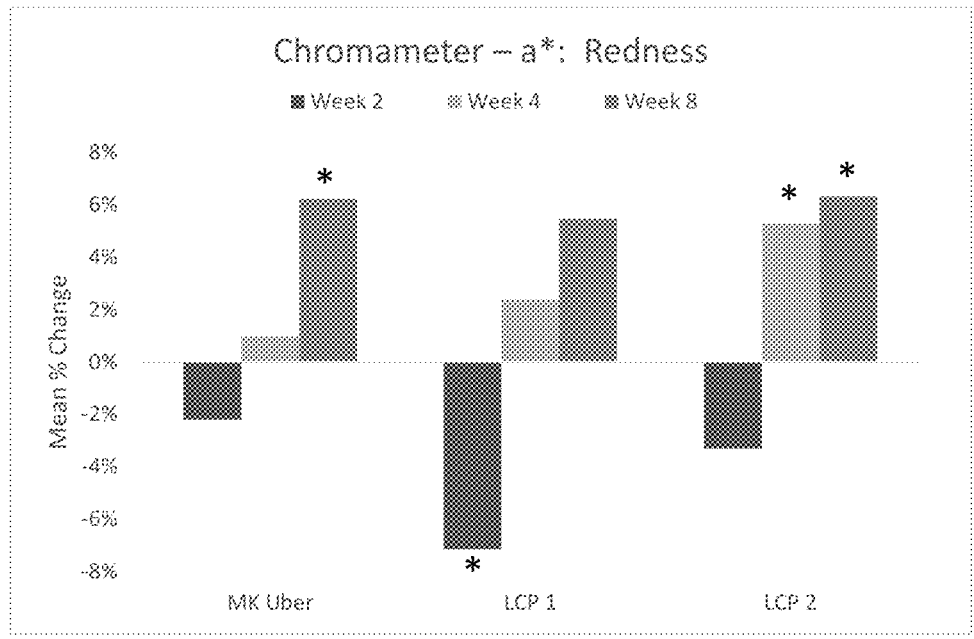
FIG. 4 shows results for skin redness using a chromameter as a measurement tool. Data indicated by an * is statistically significant compared to Baseline values.

Lightness, shown in FIG. 3, and redness in skin, shown in FIG. 4, were measured using a chromameter at the end of Week 2, Week 4, and Week 8, which were compared to Baseline measurements. FIGS. 3 and 4 show the average percentage improvement over baseline for each test product. For skin lightness, MK Uber, LCP 1, and LCP 2 showed significant improvement in Week 4. For skin redness (reduction in redness), MK Uber showed statistically significant improvement in Week 8. LCP 2 showed statistically significant improvement in Week 4 and Week 8. LCP 1 did not show statistically significant improvement. LCP 1 showed significant worsening in redness during Week 2.

Figure 5:
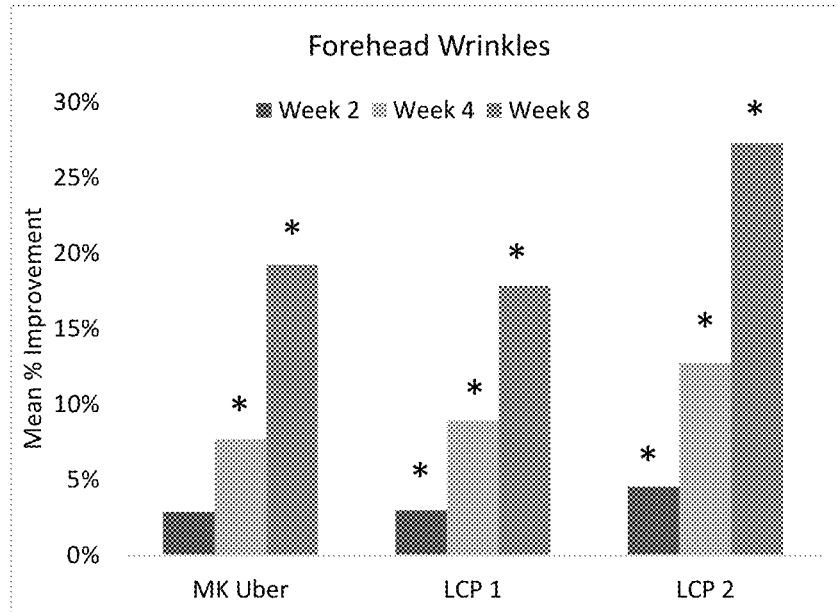
FIG. 5 shows results for reduction of forehead wrinkles as scored on a Dermatologist Scale from 0 to 9 (best to worst). Data indicated by an * is statistically significant compared to Baseline values.
Figure 6:
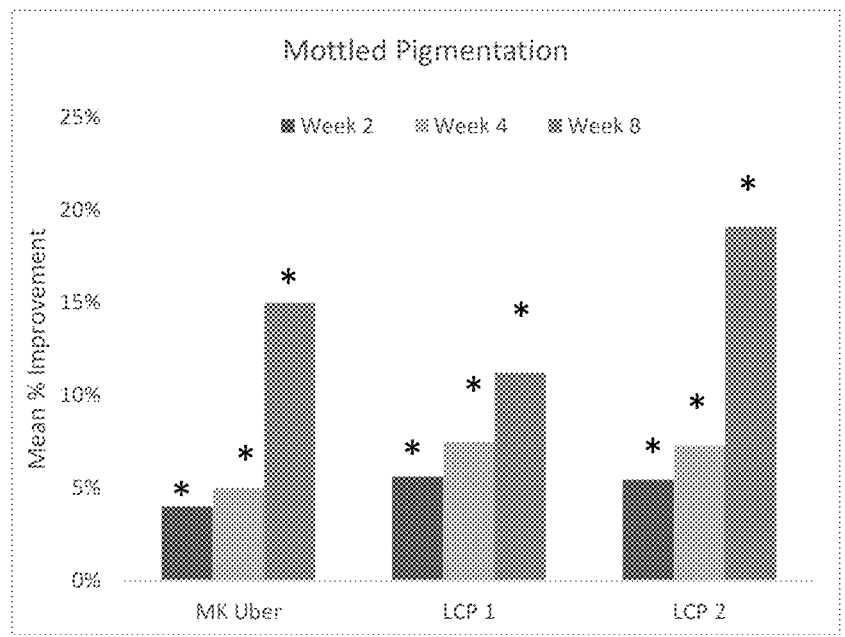
FIG. 6 shows results for reduction of mottled pigmentation in skin as scored on a Dermatologist Scale from 0 to 9 (best to worst). Data indicated by an * is statistically significant compared to Baseline values.
Figure 7:
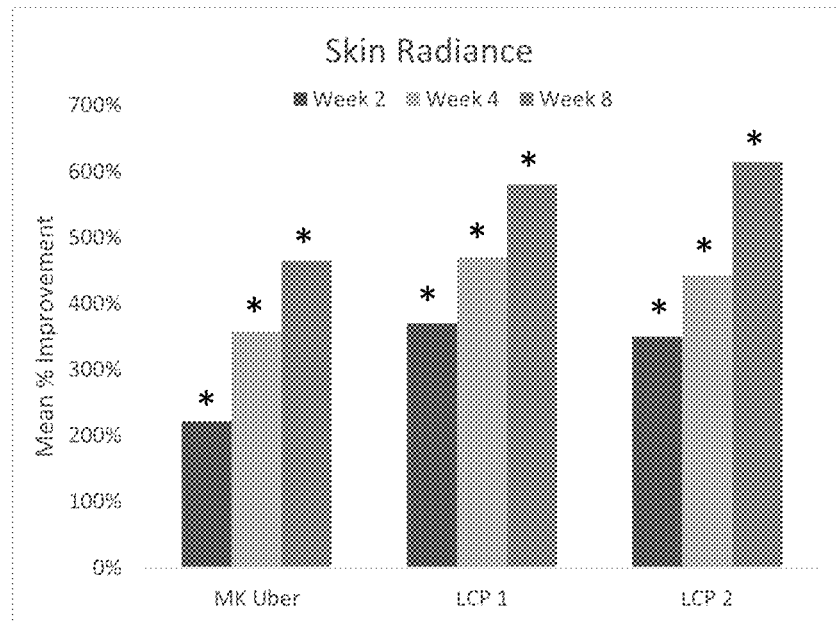
FIG. 7 shows results for increase in skin radiance as scored on a Dermatologist Scale from 0 to 9 (worst to best). Data indicated by an * is statistically significant compared to Baseline values.

Some signs of ageing and skin damage include increase in forehead wrinkles, increase in mottled pigmentation, and decrease in skin radiance. Forehead wrinkles, pigmentation, and skin radiance were scored on a ten (10) point scale at the end of Week 2, Week 4, and Week 8, which were compared to Baseline measurements. For forehead wrinkles and pigmentation, a score of 0 was considered the best and a score of 9 was considered the worst because a reduction in forehead wrinkles and/or pigmentation showed improvement. For skin radiance, a score of 0 was considered the worst and a score of 9 was considered the best because an increase in skin radiance showed improvement. FIGS. 5, 6, and 7 show the average percentage improvement in forehead wrinkles (reduction of forehead wrinkles), in pigmentation (reduction in mottled pigmentation), and in skin radiance (increase in skin radiance), respectively, as scored in clinical grading, for each test product. For forehead wrinkles, MK Uber showed significant percentage improvement in Week 4 and Week 8. LCP 1 and LCP 2 showed significant improvement in Week 2, Week 4, and Week 8. For pigmentation, MK Uber, LCP 1, and LCP 2 showed statistically significant improvement in Week 2, Week 4, and Week 8. For skin radiance, MK Uber, LCP 1, and LCP 2 showed statistically significant improvement in Week 2, Week 4, and Week 8. Specifically, MK Uber showed an over 400% improvement in skin radiance over the Baseline. MK Uber showed a visible improvement in wrinkles.

Figure 8:
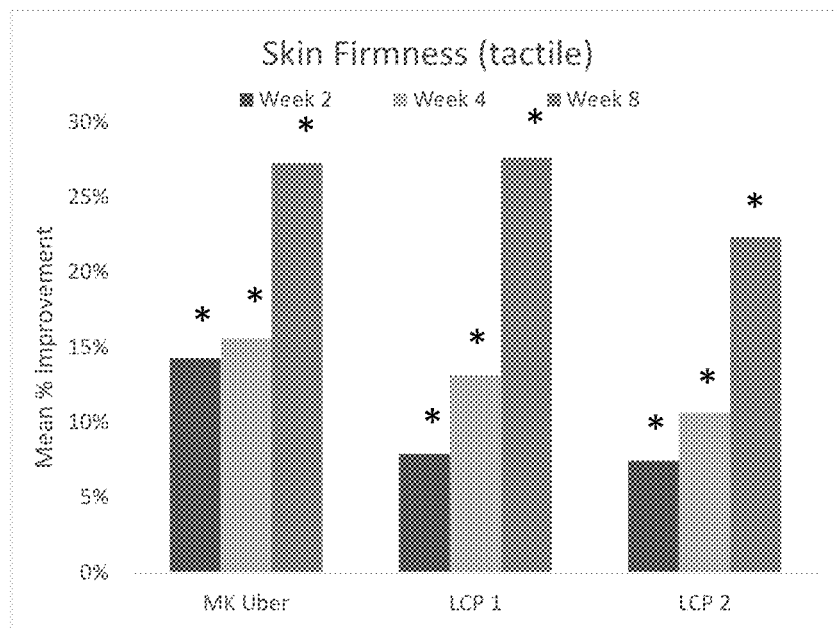
FIG. 8 shows results for increase in skin firmness as a tactile measure as scored on a Dermatologist Scale from 0 to 9 (worst to best). Data indicated by an * is statistically significant compared to Baseline values.
Figure 9:
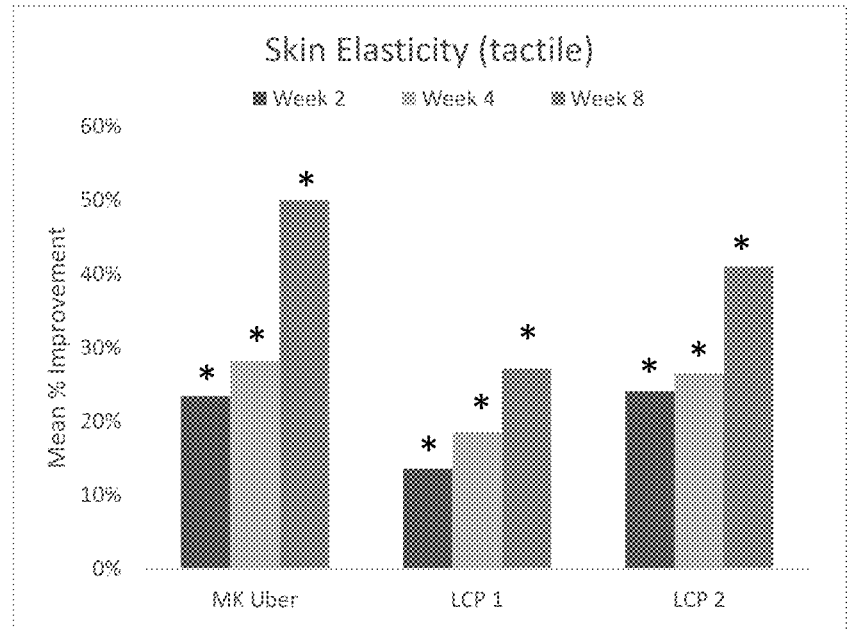
FIG. 9 shows results for increase in skin elasticity as a tactile measure as scored on a Dermatologist Scale from 0 to 9 (worst to best). Data indicated by an * is statistically significant compared to Baseline values.

Other signs of ageing and skin damage include decrease in skin firmness and decrease in skin elasticity. Skin firmness and skin elasticity were scored on a ten (10) point scale at the end of Week 2, Week 4, and Week 8, which were compared to Baseline measurements. For skin firmness and skin elasticity, a score of 0 was considered the worst and a score of 9 was considered the best because an increase in skin firmness and/or skin elasticity showed improvement. Skin firmness and skin elasticity were clinically graded using tactile means. FIGS. 8 and 9 show the average percentage improvement in skin firmness (increase in skin firmness) and in skin elasticity (increase in skin elasticity), respectively, as scored in clinical grading, for each test product. For skin firmness, MK Uber, LCP 1, and LCP 2 showed significant percentage improvement in Week 2, Week 4, and Week 8. For skin elasticity, MK Uber, LCP 1, and LCP 2 showed statistically significant improvement in Week 2, Week 4, and Week 8.

Figure 10:
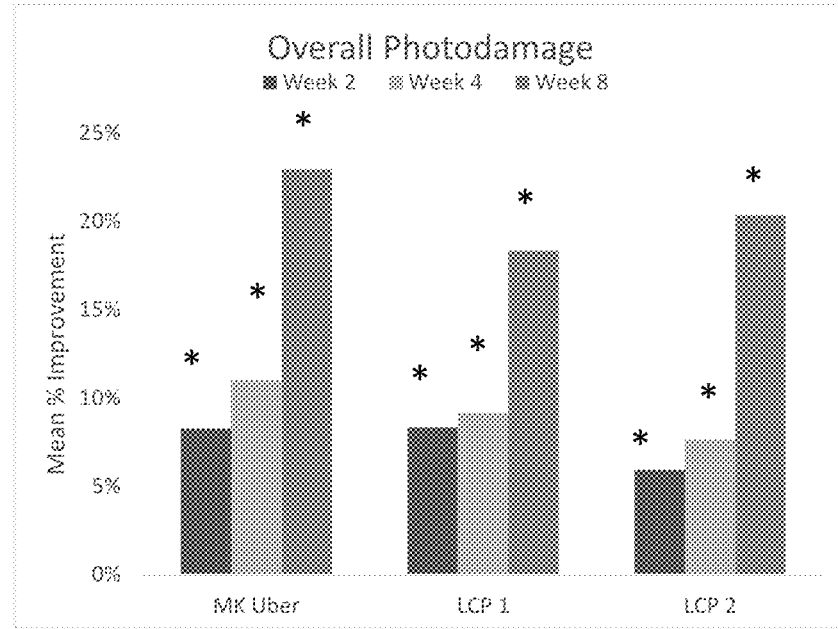
FIG. 10 shows results for reduction in overall photodamage as scored on a Dermatologist Scale from 0 to 9 (best to worst). Data indicated by an * is statistically significant compared to Baseline values.
Figure 11:
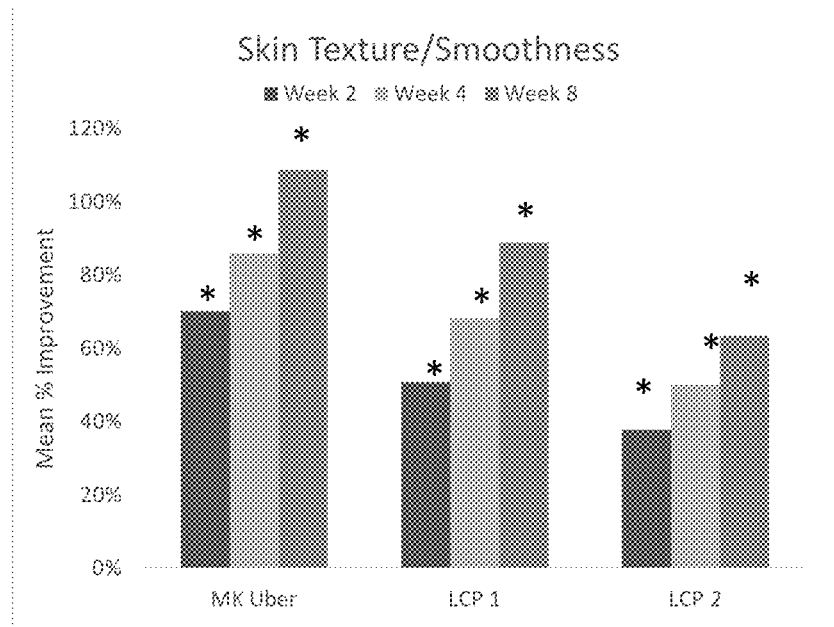
FIG. 11 shows results for improvement in skin texture/smoothness as scored on a Dermatologist Scale from 0 to 9 (worst to best). Data indicated by an * is statistically significant compared to Baseline values.
Figure 12:
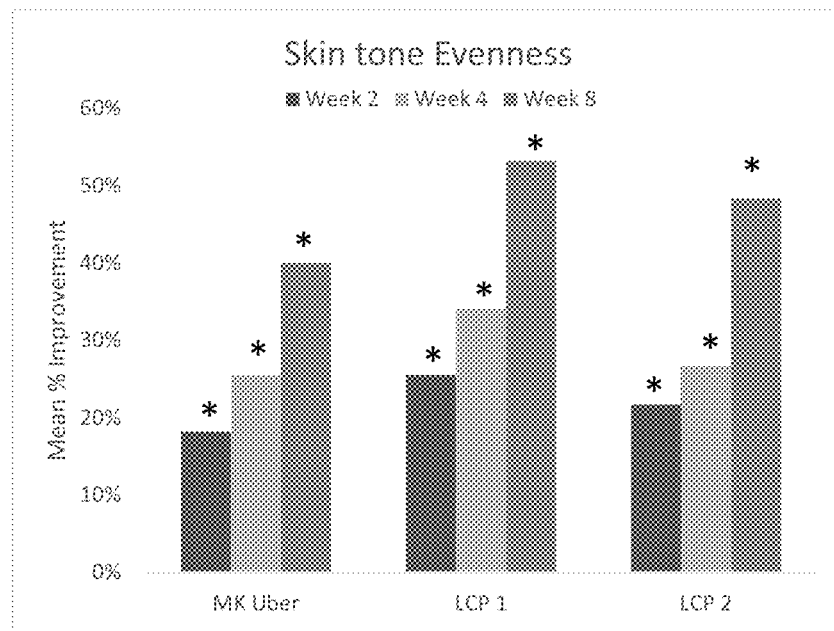
FIG. 12 shows results for increase in skin tone evenness as scored on a Dermatologist Scale from 0 to 9 (worst to best). Data indicated by an * is statistically significant compared to Baseline values.

Additional signs of ageing and skin damage include increase in overall photodamage, decrease in skin texture/smoothness, and decrease in skin tone evenness. Overall skin photodamage, skin smoothness, and skin tone evenness were scored on a ten (10) point scale at the end of Week 2, Week 4, and Week 8, which were compared to Baseline measurements. For overall photodamage, a score of 0 was considered the best and a score of 9 was considered the worst because a reduction in overall skin photodamage showed improvement. For skin smoothness and skin tone evenness, a score of 0 was considered the worst and a score of 9 was considered the best because an increase in skin smoothness and/or skin tone evenness showed improvement. FIGS. 10, 11, and 12 show the average percentage improvement in overall photodamage (decrease in overall skin photodamage), in skin texture/smoothness (increase in skin smoothness), and in skin tone evenness (increase in skin tone evenness), respectively, as scored in clinical grading, for each test product. For overall photodamage, MK Uber, LCP 1, and LCP 2 showed significant percentage improvement in Week 2, Week 4, and Week 8. For skin texture/smoothness, MK Uber, LCP 1, and LCP 2 showed statistically significant improvement in Week 2, Week 4, and Week 8. For skin tone evenness, MK Uber, LCP 1, and LCP 2 showed statistically significant improvement in Week 2, Week 4, and Week 8. MK Uber showed an over 100% improvement in skin smoothness over the Baseline. MK Uber showed a visible improvement in skin tone.

Dermatologist Tolerance was measured for erythema/redness, dryness, peeling/flaking, and irritation in skin, and Self-Assessment Tolerance was collected for burning, stinging, itching, and tingling sensations in skin. Dermatologist Tolerance and Self-Assessment Tolerance were scored with an effect of "none," "mild," "moderate," or "high." No scores were at "mild" or above.

C. Example 3 (In-Vitro Efficacy of Ingredients)

It has been determined that *Rosmarinus officianalis* leaf extract, *Morus alba* fruit extract, tetrahexyldecyl ascorbate, retinol, *Acmella oleracea* extract, *Alpinia galanga* leaf extract, *Argania spinosa* oil, and/or saccharide isomerate can increase anti-oxidant capacity (TEAC) in skin, increase collagen expression in skin, increase elastin expression in skin, increase laminin expression in skin, inhibit MMP-1, inhibit MMP-3, inhibit MMP-9, inhibit pro-inflammatory cytokines (e.g., lipoxygenase, IL-6, Il-8, TNF-α, or VEGF), inhibit elastase expression in skin, and/or increase fibronectin expression in skin. A summary of results are found in Tables 2 to 9 and the methods used to determine the properties of the ingredients are provided below.

TABLE 2

(Change in Expression of Activities)

| Type of Change | Ingredient | Change (%) |
|---|---|---|
| Increase Anti-Oxidant (AO) Capacity | *Rosmarinus officianalis* leaf extract | 52 |
| | *Acmella oleracea* extract | 80 |
| | *Morus alba* fruit extract | 98 |
| Increase Collagen Expression | *Acmella oleracea* extract | 41 |
| | *Morus alba* fruit extract | 27 |
| | *Alpinia galanga* leaf extract | 25 |
| | *Argania spinosa* kernel extract | 28 |
| | Tetrahexyldecyl ascorbate | 50 |
| Increase Elastin Expression | *Alpinia galanga* leaf extract | 43 |
| | *Argania spinosa* kernel extract | 82 |
| Increase Laminin Expression | *Acmella oleracea* extract | 39 |
| | *Morus alba* fruit extract | 14 |
| | *Alpinia galanga* leaf extract | 500 |
| | *Argania spinosa* kernel extract | 135 |
| Inhibit MMP-1 | *Rosmarinus officianalis* leaf extract | 98 |
| | *Morus alba* fruit extract | 96 |
| Inhibit MMP-3 | *Rosmarinus officianalis* leaf extract | 40 |
| | *Morus alba* fruit extract | 29 |
| | Tetrahexyldecyl ascorbate | 38 |
| Inhibit MMP-9 | *Rosmarinus officianalis* leaf extract | 61 |
| | *Acmella oleracea* extract | 80 |
| | *Morus alba* fruit extract | 84 |
| | Tetrahexyldecyl ascorbate | 11 |
| Inhibit Lipoxygenase | *Rosmarinus officianalis* leaf extract | 54 |
| | *Acmella oleracea* extract | 98 |
| Inhibit IL-6 | *Rosmarinus officianalis* leaf extract | 83 |
| | *Acmella oleracea* extract | 80 |
| | Tetrahexyldecyl ascorbate | 38 |
| Inhibit IL-8 | *Rosmarinus officianalis* leaf extract | 98 |
| Inhibit TNF-α | *Rosmarinus officianalis* leaf extract | 85 |
| | Saccharide Isomerate | 88 |
| Inhibit VEGF | *Rosmarinus officianalis* leaf extract | 50 |
| Inhibit Elastase | *Rosmarinus officianalis* leaf extract | 54 |
| | *Morus alba* fruit extract | 25 |
| Increase Fibronectin Expression | *Morus alba* fruit extract | 13 |
| | *Argania spinosa* kernel extract | 22 |

Antioxidant (AO) Assay: *Rosmarinus officianalis* leaf extract, *Acmella oleracea* extract, and *Morus alba* fruit extract have been shown to provide anti-oxidant capacity (TEAC) by inhibiting the oxidation of ABTS® (2,2'-azino-di-[3-ethylbenzthiazoline sulphonate]) to ABTS®+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of *Rosmarinus officianalis* leaf extract, *Acmella oleracea* extract, and *Morus alba* fruit extract to prevent ABTS oxidation was compared with that of Trolox, a water-soluble tocopherol analogue, and was quantified as molar Trolox equivalents. Anti-Oxidant capacity kit #709001 from Cayman Chemical (Ann Arbor, Michigan USA) was used to measure the total anti-oxidant capacity. It was determined that *Rosmarinus officianalis* leaf extract inhibited the oxidation of ABTS® to ABTS®+ by metmyoglobin by 52%, *Acmella oleracea* extract inhibited by 80%, and *Morus alba* fruit extract inhibited by 98% as compared to the inhibition of oxidation by Trolox.

Collagen Stimulation Assay: *Acmella oleracea* extract, *Morus alba* fruit extract, *Alpinia galanga* leaf extract, *Argania spinosa* kernel extract, and tetrahexyldecyl ascorbate have been shown to increase expression of procollagen-1, a precursor to collagen. Collagens (types I, II, III, IV and V) are synthesized as precursor molecules called procollagens. These precursor molecules contain additional peptide sequences, usually called "propeptides", at both the amino-terminal and the carboxy-terminal ends. During cellular expression and secretion, procollagens are assembled in the trimeric form and then cleaved at specific N- and C-terminal sites by specific endopeptidases, generating three fragments: procollagen-1 N-terminal propeptide (PINP), Type I collagen, and procollagen-1 carboxy-terminal propeptide (PICP).

The function of the propeptides is to facilitate the winding of procollagen molecules into a triple-helical conformation within the endoplasmic reticulum. The propeptides are cleaved off from the collagen triple helix molecule during its secretion, after which the triple helix collagens polymerize into extracellular collagen fibrils. Thus, the amount of the free propeptides reflects stoichiometrically the amount of collagen molecules synthesized (a relationship analogous to that between the carboxy-terminal peptide of proinsulin and the endogenously produced insulin). Collagen is an extracellular matrix protein critical for skin structure. Increased synthesis of collagen helps improve skin firmness and elasticity. MK Uber showed a visible improvement in skin firmness.

Quantitative detection of PICP in fibroblast cell extracts and culture supernatants was performed with an enzyme immunoassay kit (e.g., Takara #MK101) to assess the effects of the ingredients on the synthesis of PICP in skin. This bioassay was used to examine effects on the production of procollagen peptide (a precursor to collagen) by human epidermal fibroblasts. The endpoint of this assay was a spectrophotometric measurement that reflects the presence of procollagen peptide and cellular viability. The assay employed the quantitative sandwich enzyme immunoassay technique whereby a monoclonal antibody specific for procollagen peptide was pre-coated onto a microplate. Standards and samples were pipetted into the wells and any procollagen peptide present was bound by the immobilized antibody. After washing away any unbound substances, an enzyme-linked polyclonal antibody specific for procollagen peptide was added to the wells. Following a wash to remove any unbound antibody-enzyme reagent, a substrate solution was added to the wells and color was developed in proportion to the amount of procollagen peptide bound in the initial step. Color development was stopped and the intensity of the color at 450 nm was measured using a microplate reader. It was determined that *Acmella oleracea* extract increased procollagen-1 expression by 41%, *Morus alba* fruit extract increased procollagen-1 expression by 27%, *Alpinia galanga* leaf extract increased procollagen-1 expression by 25%, *Argania spinosa* kernel extract increased procollagen-1 expression by 28%, and tetrahexyldecyl ascorbate increased procollagen-1 expression by 50%.

For generation of samples and controls, subconfluent normal human adult epidermal fibroblasts (Cascade Biologics) were cultivated in standard DMEM growth medium with 10% fetal bovine serum (Mediatech) at 37° C. in 10% $CO_2$. The cells were treated with each of the tested ingredients and controls for 3 days. Following incubation, cell culture medium was collected and the amount of Type I procollagen peptide secretion was quantified using the sandwich enzyme linked immuno-sorbant assay (ELISA) from Takara (#MK101) as explained above.

Elastin Stimulation Assay: *Alpinia galanga* leaf extract and *Argania spinosa* kernel extract have been shown to increase elastin expression. Elastin is a connective tissue protein that helps skin resume shape after stretching or contracting. Elastin is also an important load-bearing protein used in places where mechanical energy is required to be stored. Elastin is made by linking many soluble tropoelastin protein molecules, in a reaction catalyzed by lysyl oxidase. Elastin secretion and elastin fibers were monitored in cultured human fibroblasts by staining of cultured human fibroblasts using immunofluorescent antibodies directed against elastin by a direct ELISA sandwich method. A Meso Scale Discovery system SECTOR 2400 Imaging system was used to analyze the results. Changes in elastin secretion and elastin fibers caused by *Argania spinosa* kernel extract and *Alpinia galanga* leaf extract were determined by incubating cultured human fibroblasts with the active ingredient for a period of time before probing the cells or a lysate thereof with antibodies directed against elastin. It was shown that *Argania spinosa* kernel extract and *Alpinia galanga* leaf extract increased elastin synthesis by 82% and 43%, respectively.

Laminin Stimulation Assay: Laminin is a major protein in the dermal-epidermal junction (DEJ) (also referred to as the basement membrane). The DEJ is located between the dermis and the epidermis interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Laminin is a structural glycoprotein located in the DEJ. Together with fibronectin, laminin is considered the glue that holds the cells together, and both are secreted by dermal fibroblasts to help facilitate intra- and inter-cellular adhesion of the epidermal calls to the DEJ.

Laminin secretion was monitored by quantifying laminin in cell supernatants of cultured human fibroblasts treated for 3 days with culture medium with or without 1.0% final concentration of the test ingredient(s). Following incubation, laminin content was measured using immunofluorescent antibodies directed against each protein in an enzyme linked immuno-sorbant assay (ELISA). It was determined that *Acmella oleracea* extract increased laminin expression by 39%, *Morus alba* fruit extract increased laminin expression by 14%, *Alpinia galanga* leaf extract increased laminin expression by 500%, and *Argania spinosa* kernel extract increased laminin expression by 135%.

Matrix Metalloproteinase 1 Enzyme Activity (MMP-1) Assay: *Rosmarinus officianalis* leaf extract and *Morus alba* fruit extract have been shown to inhibit MMP-1 expression. MMPs are extracellular proteases that play a role in many normal and disease states by virtue of their broad substrate specificity. MMP-1 substrates include collagen IV. The Molecular Probes Enz/Chek Gelatinase/Collagenase Assay kit (#E12055), used to detect MMP-1 protease activity, utilizes a fluorogenic gelatin substrate and tests proteolytic cleavage of the substrate by purified MMP-1 enzyme. Upon proteolytic cleavage of the substrate, bright green fluorescence is revealed and was monitored using a fluorescent microplate reader to measure enzymatic activity.

Test materials were incubated in the presence or absence of the purified enzyme and substrate to determine their protease inhibitor capacity. It was determined that *Rosmarinus officianalis* leaf extract and *Morus alba* fruit extract inhibited MMP-1 by 98% and 96%, respectively.

Matrix Metalloproteinase 3 and 9 Enzyme Activity (MMP-3; MMP-9) Assay: *Rosmarinus officianalis* leaf extract, *Morus alba* fruit extract, tetrahexyldecyl ascorbate, and/or *Acmella oleracea* extract have been shown to inhibit MMP-3 and/or MMP-9 expression. MMPs are extracellular proteases that play a role in many normal and disease states by virtue of their broad substrate specificity. MMP-3 substrates include collagens, fibronectins, and laminin; while MMP-9 substrates include collagen VII, fibronectins and laminin. Colorimetric Drug Discovery kits from BioMol International for MMP-3 (AK-400) and MMP-9 (AK-410) were used to measure protease activity of MMPs using a thiopeptide as a chromogenic substrate (Ac-PLG-[2-mercapto-4-methyl-pentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\epsilon$=13,600 M-1cm-1 at pH 6.0 and above 7). It was determined that *Rosmarinus officianalis* leaf extract inhibited MMP-3 by 40%, *Morus alba* fruit extract inhibited by 29%, and tetrahexyldecyl ascorbate inhibited by 38%. It was determined that *Rosmarinus officianalis* leaf extract inhibited MMP-9 by 61%, *Morus alba* fruit extract inhibited by 84%, tetrahexyldecyl ascorbate inhibited by 11%, and *Acmella oleracea* extract inhibited by 80%.

Lipoxygenase (LO) Assay: *Rosmarinus officianalis* leaf extract and/or *Acmella oleracea* extract have been shown to inhibit lipoxygenase (LO) expression. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotrienes, potent inflammatory mediators. An accurate and convenient method for screening lipoxygenase inhibitors is performed by measuring the hydroperoxides generated from the incubation of a lipoxygenase (5-, 12-, or 15-LO) with arachidonic acid. The Colorimetric LO Inhibitor screening kit (#760700, Cayman Chemical) was used to determine the ability of *Rosmarinus officianalis* leaf extract and/or *Acmella oleracea* extract to inhibit enzyme activity.

Purified 15-lipoxygenase and test ingredients were mixed in assay buffer and incubated with shaking for 10 min at room temperature. Following incubation, arachidonic acid was added to initiate the reaction and the mixtures were incubated for an additional 10 min at room temperature. Colorimetric substrate was added to terminate catalysis and color progression was evaluated by fluorescence plate reading at 490 nm. The percent inhibition of lipoxyganse activity was calculated compared to non-treated controls to determine the ability of *Rosmarinus officianalis* leaf extract and/or *Acmella oleracea* extract to inhibit the activity of purified enzyme. It was determined that *Rosmarinus officianalis* leaf extract and/or *Acmella oleracea* extract inhibited lipoxyganse activity by 54% and 98%, respectively.

Tumor Necrosis Factor Alpha (TNF-$\alpha$) Assay: *Rosmarinus officianalis* leaf extract and saccharide isomerate inhibit TNF-$\alpha$ activity. The prototype ligand of the TNF superfamily, TNF-$\alpha$, is a pleiotropic cytokine that plays a central role in inflammation. Increase in its expression is associated with an up regulation in pro-inflammatory activity. The bioassay used analyzed the effect of *Rosmarinus officianalis* leaf extract and saccharide isomerate on the production of TNF-$\alpha$ by human epidermal keratinocytes. The endpoint of this assay was a spectrophotometric measurement that reflects the presence of TNF-$\alpha$ and cellular viability. The assay employed the quantitative sandwich enzyme immunoassay technique whereby a monoclonal antibody specific for TNF-$\alpha$ had been pre-coated onto a microplate.

Standards and samples were pipetted into wells of the microplate and any TNF-$\alpha$ present was bound by the immobilized antibody. After washing away any unbound substances, an enzyme-linked polyclonal antibody specific for TNF-$\alpha$ was added to the wells. Following a wash to remove any unbound antibody-enzyme reagent, a substrate solution was added to the wells and color developed in proportion to the amount of TNF-$\alpha$ bound in the initial step using a microplate reader for detection at 450 nm. The color development can be stopped and the intensity of the color was measured. Subconfluent normal human adult keratinocytes (Cascade Biologics) cultivated in EPILIFE™ standard growth medium (Cascade Biologics) at 37° C. in 5% $CO_2$ were treated with phorbol 12-myristate 13-acetate (PMA, 10 ng/ml, Sigma Chemical, #P1585-1MG) and *Rosmarinus officianalis* leaf extract, saccharide isomerate, or no test ingredient (for negative control) for 6 hours. PMA has been shown to cause a dramatic increase in TNF-$\alpha$ secretion which peaks at 6 hours after treatment. Following incubation, cell culture medium was collected and the amount of TNF-$\alpha$ secretion quantified using a sandwich enzyme linked immuno-sorbant assay (ELISA) from R&D Systems (#DTA00C). *Rosmarinus officianalis* leaf extract and saccharide isomerate inhibit TNF-$\alpha$ by 85% and 88%, respectively.

Elastase Assay: ENZCHEK® Elastase Assay (Kit #E-12056) from Molecular Probes (Eugene, Oregon USA) was used as an in vitro enzyme inhibition assay for measuring inhibition of elastase activity in the presence of *Rosmarinus officianalis* leaf extract and *Morus alba* fruit extract. The EnzChek kit contained soluble bovine neck ligament elastin that is labeled with dye such that the conjugate's fluorescence is quenched. The non-fluorescent substrate was digested by elastase or other proteases to yield highly fluorescent fragments. The resulting increase in fluorescence was monitored with a fluorescence microplate reader. Digestion products from the elastin substrate have absorption maxima at ~505 nm and fluorescence emission maxima at ~515 nm. The peptide, N-methoxysuccinyl-Ala-Ala-Pro-Val-chloromethyl ketone, was used as a selective, collective inhibitor of elastase for a positive control when utilizing the EnzChek Elastase Assay Kit for screening for elastase inhibitors. It was determined that *Rosmarinus officianalis* leaf extract and *Morus alba* fruit extract inhibited elastase by 54% and 25%, respectively.

Fibronectin Stimulation Assay: Fibronectin is a major protein in the dermal-epidermal junction (DEJ) (also referred to as the basement membrane). The DEJ is located between the dermis and the epidermis interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Fibronectin is a structural glycoprotein located in the DEJ. Together with laminin, fibronectin is considered the glue that holds the cells together, and both are secreted by dermal fibroblasts to help facilitate intra- and inter-cellular adhesion of the epidermal calls to the DEJ.

Fibronectin secretion was monitored by quantifying fibronectin in cell supernatants of cultured human fibroblasts treated for 3 days with culture medium with or without 1.0% final concentration of the test ingredient(s). Following incubation, fibronectin content was measured using immunofluorescent antibodies directed against each protein in an enzyme linked immuno-sorbant assay (ELISA). It was determined that *Argania spinosa* kernel extract and *Morus alba* fruit extract increased fibronectin expression by 22% and 13%, respectively.

D. Example 4 (Exemplary Formulations)

Formulations having the ingredients disclosed herein were prepared as topical skin compositions. In some instances, the topical skin compositions can be prepared as an emulsion, serum, gel, gel emulsion, or cream. The formulation in Table 3 is an example of a topical skin composition prepared as a cream.

TABLE 3^

| Ingredient | % Concentration (by weight) |
| --- | --- |
| Water | 65.5 |
| Caprylic/Capric Triglyceride | 6 |
| Glycerin | 6 |
| Pentylene glycol | 3.1 |
| Tetrahexyldecyl ascorbate | 3 |
| Ammonium acryloyldimethyltaurate/VP copolymer | 2 |
| Dimethicone | 2 |
| *Argania spinosa* kernel oil | 1.9 |
| Propanediol | 1.7 |
| Sodium phytate | 1.5 |
| Triethanolamine | 1.3 |
| Silica | 1 |
| Lactic acid | 0.8 |
| Betaine | 0.7 |
| Phenoxyethanol | 0.5 |
| Polysorbate 20 | 0.5 |
| Retinol | 0.5 |
| Caprylyl glycol | 0.4 |
| Polyacrylate-13 | 0.3 |
| Butylene glycol | 0.3 |
| *Acmella oleracea* extract | 0.2 |
| Tocopheryl acetate | 0.2 |
| BHT | 0.1 |
| Polyisobutene | 0.1 |
| *Alpinia galanga* leaf extract | 0.1 |
| *Rosmarinus offinalis* (Rosemary) leaf extract | 0.04 |

TABLE 3^-continued

| Ingredient | % Concentration (by weight) |
| --- | --- |
| Saccharide isomerate | 0.02 |
| *Morus alba* fruit extract | 0.003 |
| Excipients* | q.s. |

^Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition or ingredients that provide benefits to skin.
*Excipients can be added, for example, to modify the rheological properties of the composition. Alternatively, the amount of water can be varied so long as the amount of water in the composition is at least 40% w/w, and preferably between 50 to 80% w/w.

In some instances, the topical skin compositions can be prepared as a facial milk, calming milk, or serum. The formulation in Table 4 is an example of a topical skin composition prepared as a facial milk.

TABLE 4^

| Ingredient | % Concentration (by weight) |
| --- | --- |
| Water | 63 |
| Caprylic/Capric Triglyceride | 6.5 |
| Glycerin | 6 |
| Pentylene glycol | 3.1 |
| Tetrahexyldecyl ascorbate | 3 |
| Ammonium acryloyldimethyltaurate/VP copolymer | 2.5 |
| Dimethicone | 2 |
| *Argania spinosa* kernel oil | 1.9 |
| Propanediol | 1.7 |
| Glyceryl oleate citrate | 1.5 |
| Sodium phytate | 1.5 |
| Triethanolamine | 1.3 |
| Silica | 1 |
| Lactic acid | 0.8 |
| Betaine | 0.7 |
| Polysorbate 20 | 0.5 |
| Retinol | 0.5 |
| Phenoxyethanol | 0.5 |
| Caprylyl glycol | 0.4 |
| Polyacrylate-13 | 0.3 |
| Butylene glycol | 0.3 |
| *Acmella oleracea* extract | 0.2 |
| Tocopheryl acetate | 0.2 |
| Polyisobutene | 0.1 |
| *Alpinia galanga* leaf extract | 0.1 |
| *Rosmarinus offinalis* (Rosemary) leaf extract | 0.04 |
| Saccharide isomerate | 0.02 |
| *Morus alba* fruit extract | 0.003 |
| Excipients* | q.s. |

^Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition or ingredients that provide benefits to skin.
*Excipients can be added, for example, to modify the rheological properties of the composition. Alternatively, the amount of water can be varied so long as the amount of water in the composition is at least 40% w/w, and preferably between 50 to 80% w/w.

E. Example 5 (Use Examples)

Some uses of a topical skin composition including a combination of *Rosmarinus officianalis* leaf extract, *Morus alba* fruit extract, tetrahexyldecyl ascorbate, *Acmella oleracea* extract, *Alpinia galanga* leaf extract, *Argania spinosa* oil, saccharide isomerate, and less than 1 wt. % retinol to treat skin have been identified. Treatment methods can include various application instructions and/or combinations of compositions, facial milks, sunscreens, cleansers, day cream, night cream, serums, gels, or other skin treatment products.

In some instances, for skin that has not been exposed to retinol solutions or sensitive skin, a topical composition as disclosed herein and a facial milk as disclosed herein can be used to provide one or more anti-aging benefits to skin. According to some implementations, a topical skin composition as disclosed herein and a facial milk as disclosed herein can be used over an at least eight week period to improve skin. During Weeks 1 and 2, the skin can be cleansed in the evening. After 5-10 minutes pass, once per week, a pea-sized amount of a topical composition comprising any one of, any combination of, or all of *Rosmarinus officianalis* leaf extract, *Morus alba* fruit extract, tetrahexyldecyl ascorbate, retinol, *Acmella oleracea* extract, *Alpinia galanga* leaf extract, *Argania spinosa* oil, and/or saccharide isomerate can be combined with a pea-sized amount of a facial milk comprising retinol, *Simmondsia chinensis* (jojoba) seed oil, *Cocos nucifera* (coconut) oil, *Carthamus tinctorius* (safflower) seed oil, *Olea europaea* (olive) fruit oil, and squalene. The pea-sized amounts of the topical composition and facial milk can be mixed together, used at the same time, or used one after the other. In some implementations, the mixture can be applied to the forehead, cheeks, nose, and chin in an upward, outward motion, avoiding the eye area. During Weeks 3-8, the skin can be cleansed in the evening. After 5-10 minutes pass, once per week, a pea-sized amount of a topical composition comprising any one of, any combination of, or all of *Rosmarinus officianalis* leaf extract, *Morus alba* fruit extract, tetrahexyldecyl ascorbate, retinol, *Acmella oleracea* extract, *Alpinia galanga* leaf extract, *Argania spinosa* oil, and/or saccharide isomerate can be applied to the forehead, cheeks, nose, and chin and then smoothed on the entire face in an upward, outward motion, avoiding the eye area. Then, a pea-sized amount of a facial milk comprising retinol, *Simmondsia chinensis* (jojoba) seed oil, *Cocos nucifera* (coconut) oil, *Carthamus tinctorius* (safflower) seed oil, *Olea europaea* (olive) fruit oil, and squalene can be applied to the forehead, cheeks, nose, and chin and then smoothed on the entire face in an upward, outward motion, avoiding the eye area. During Weeks 3-4, this procedure can be followed once per week. During Weeks 5-6, this procedure can be followed twice per week. During Weeks 7-8, this procedure can be followed three to five times per week. During Weeks 1-8, the facial milk composition can be used at any point in the day and as needed to relieve irritated skin. In some preferred implementations, sunscreen can be used during the day.

In some instances, for skin that has previously been exposed to retinol solutions or non-sensitive skin, a topical composition as disclosed herein and a facial milk as disclosed herein can be used to provide one or more anti-aging benefits to skin. According to some implementations, a topical skin composition as disclosed herein and a facial milk as disclosed herein can be used over an at least eight week period to improve skin. A pea-sized amount of a topical composition comprising any one of, any combination of, or all of *Rosmarinus officianalis* leaf extract, *Morus alba* fruit extract, tetrahexyldecyl ascorbate, retinol, *Acmella oleracea* extract, *Alpinia galanga* leaf extract, *Argania spinosa* oil, and/or saccharide isomerate can be applied to clean, dry skin every other evening, gradually increasing frequency after Week 2 as tolerated by skin. In some implementations, the pea-sized amount can be applied to the forehead, cheeks, nose, and chin in an upward, outward motion, avoiding the eye area. In some implementations, the topical composition can be combined with a pea-sized amount of a facial milk comprising retinol, *Simmondsia chinensis* (jojoba) seed oil, *Cocos nucifera* (coconut) oil, *Carthamus tinctorius* (safflower) seed oil, *Olea europaea* (olive) fruit oil, and squalene. The pea-sized amounts of the topical composition and facial milk can be mixed together, used at the same time, or used one after the other. In some implementations, the user will allow for full absorption of the topical composition before applying additional skin products. In some preferred implementations, sunscreen can be used during the day.

F. Example 6 (Additional Assays)

Assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

Lysyl Oxidase Assay: A lysyl oxidase assay can be performed on skin cells (e.g., epidermal keratinocytes, fibroblasts, and/or dermal endothelial cells) to determine the ability of any one of the active ingredients, combination of ingredients, or compositions having said combinations disclosed in the specification to stimulate expression of lysyl oxidase in skin. Lysyl oxidase can catalyze crosslinking of elastin and collagens, thereby providing for a more structurally rigid matrix for skin. By increasing expression of lysyl oxidase, increased cross-linking of elastin and collagens can occur, which can be beneficial in reducing the appearance of fine lines, wrinkles, sagging skin, and/or non-elastic skin.

B16 Pigmentation Assay: Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay can utilize B16-F1 melanocytes (ATCC), an immortalized mouse melanoma cell line, to analyze the effect of compounds on melanogenesis. The endpoint of this assay can be a spectrophotometric measurement of melanin production and cellular viability. B16-F1 melanocytes, can be cultivated in standard DMEM growth medium with 10% fetal bovine serum (Mediatech) at 37° C. in 10% $CO_2$ and then treated with any one of the active ingredients, combination of ingredients, or compositions having said combinations disclosed in the specification for 6 days. Following incubation, melanin secretion can be measured by absorbance at 405 nm and cellular viability is quantified.

ORAC Assay: Oxygen Radical Absorption (or Absorbance) Capacity (ORAC) of any one of the active ingredients, combination of ingredients, or compositions having said combinations disclosed in the specification can also be assayed by measuring the antioxidant activity of such ingredients or compositions. Antioxidant activity indicates a capability to reduce oxidizing agents (oxidants). This assay quantifies the degree and length of time it takes to inhibit the action of an oxidizing agent, such as oxygen radicals, that are known to cause damage to cells (e.g., skin cells). The ORAC value of any one of the active ingredients, combination of ingredients, or compositions having said combinations disclosed in the specification can be determined by methods known to those of ordinary skill in the art (see U.S. Publication Nos. 2004/0109905 and 2005/0163880; and commercially available kits such as Zen-Bio ORAC Antioxidant Assay kit (#AOX-2)). The Zen-Bio ORAC Antioxidant Assay kit measures the loss of fluorescein fluorescence over time due to the peroxyl-radical formation by the breakdown of AAPH (2,2'-axobis-2-methyl propanimidamide, dihydrochloride). Trolox, a water soluble vitamin E analog, serves as positive control inhibition fluorescein decay in a dose dependent manner.

Production of Hyaluronic Acid: Changes in the production of hyaluronic acid (HA) in human dermal fibroblasts due to each of the active ingredients, any one of the combination of ingredients, or compositions having said combinations disclosed in the specification can be measured. HA is a polysaccharide involved in stabilization of the structure of the matrix and is involved in providing turgor pressure to tissue and cells. As one non-limiting example, HA production in treated and non-treated adult human dermal fibroblasts (HDFa) cells can be determined using the Hyaluronan DuoSet ELISA kit from R&D Systems (DY3614). In this assay, for production of samples, subconfluent HDFa cells from Cascade Biologics (C-13-5C) are incubated at 37° C. and 10% C02 in starvation medium (0.15% fetal bovine serum and 1% Penicillin Streptomycin solution in Dulbecco's Modified Eagle Medium) for 72 hours prior to treatment. The cells are then incubated with fresh starvation medium with either test compound, positive control (phorbol 12-myristate 13-acetate from Sigma-Aldrich (P1585) and platelet derived growth factor from Sigma-Aldrich (P3201)), or no additive for 24 hours. Media is then collected and frozen at −80° C. until use in the ELISA assay.

Briefly, the ELISA assay employs a quantitative sandwich enzyme immunoassay technique whereby a capture antibody specific for HA can be pre-coated onto a microplate. Standards and media from treated and untreated cells are pipetted into the microplate wells to enable any HA present to be bound by the immobilized antibody. After washing away any unbound substances, an enzyme-linked detection antibody specific for HA is added to the wells. Following a wash to remove any unbound antibody-enzyme reagent, a substrate solution is added to the wells to allow color development in proportion to the amount of HA bound in the initial step. The color development is stopped at a specific time and the intensity of the color at 450 nm can be measured using a microplate reader.

Production of Occludin: Changes in the production of occludin in keratinocytes due to each of the active ingredients, any one of the combination of ingredients, or compositions having said combinations disclosed in the specification can be measured. Occludin is a protein critical to the formulation of tight junctions and the skin's moisture barrier function. A non-limiting example of how occludin production in treated and non-treated keratinocytes can be determined is by the use of a bioassay that analyzes occludin concentration in keratinocyte cell lysates. The bioassay can be performed using PROTEINSIMPLE® SIMON™ western blotting protocol. For the samples, adult human epidermal keratinocytes (HEKa) from Life Technologies (C-005-5C) can be grown at 37° C. and 5% CO2 for 24 hours in EPILIFE™ growth media with calcium from Life Technologies (M-EP-500-CA) supplemented with Keratinocyte Growth Supplement (HKGS) from Life Technologies (S-101-5). HEKa are then incubated in growth medium with test compound/extract, no compound/extract for negative control, or with 1 mM $CaCl_2$ for positive control for 24 to 48 hours. The HEKa are then washed, collected, and stored on ice or colder until lysed on ice using a lysis buffer and sonication. The protein concentrations of the samples can be determined and used to normalize the samples. The lysates are stored at −80° C. until use in the bioassay.

The PROTEINSIMPLE® SIMON™ western blotting bioassay assay employs a quantitative western blotting immunoassay technique using an antibody specific for occludin to quantitatively detect occludin in the test samples. Cell samples are lysed and normalized for protein concentration. Normalized samples and molecular weight standards are then loaded and ran on a denatured protein separation gel using capillary electrophoresis. The proteins in the gel are then immobilized and immunoprobed using a primary antibody specific for occludin. The immobilized proteins are immunoprobed with an enzyme-linked detection antibody that binds the primary antibody. A chemiluminescent substrate solution is then added to the immobilized proteins to allow chemiluminescent development in proportion to the amount of occludin bound in the immobilization. The chemiluminescent development can be stopped at a specific time and the intensity of the chemiluminescent signal can be measured and compared to positive and negative controls.

Keratinocyte Monolayer Permeability: Changes in the permeability of a keratinocyte monolayer due to each of the active ingredients, any one of the combination of ingredients, or compositions having said combinations disclosed in the specification can be measured. Keratinocyte monolayer permeability is a measure of skin barrier integrity. Keratinocyte monolayer permeability in treated and non-treated keratinocytes can be determined using, as a non-limiting example, the In Vitro Vascular Permeability assay by Millipore (ECM642). This assay analyzes endothelial cell adsorption, transport, and permeability. Briefly, adult human epidermal keratinocytes from Life Technologies (C-005-5C) can be seeded onto a porous collagen-coated membrane within a collection well. The keratinocytes are then incubated for 24 hours at 37° C. and 5% $CO_2$ in Epilife growth media with calcium from Life Technologies (M-EP-500-CA) supplemented with Keratinocyte Growth Supplement (HKGS) from Life Technologies (S-101-5). This incubation time allows the cells to form a monolayer and occlude the membrane pores. The media is then replaced with fresh media with (test sample) or without (non-treated control) test compounds/extracts and the keratinocytes are incubated for an additional 48 hours at 37° C. and 5% $CO_2$. To determine permeability of the keratinocyte monolayer after incubation with/without the test compound/extract, the media is replaced with fresh media containing a high molecular weight Fluorescein isothiocyanate (FITC)-Dextran and the keratinocytes are incubated for 4 hours at 37° C. and 5% $CO_2$. During the 4 hours incubation, FITC can pass through the keratinocytes monolayer and porous membrane into the collection well at a rate proportional to the monolayer's permeability. After the 4 hour incubation, cell viability and the content of FITC in the collection wells can be determined. For the FITC content, the media in the collection well is collected and fluorescence of the media determined at 480 nm (Em) when excited at 520 nm. Percent permeability and percent change in comparison to the non-treated controls can be determined by the following equations: Percent Permeability=((Mean Ex/Em of test sample)/Mean Ex/Em untreated control)*100; Percent Change=Percent Permeability of test sample−Percent Permeability of untreated control.

Mushroom tyrosinase activity assay: In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) can be incubated with its substrate L-Dopa (Fisher) in the presence or absence of each of the active ingredients, any one of the combination of ingredients, or compositions having said combinations disclosed in the specification. Pigment formation can be evaluated by colorimetric plate reading at 490 nm. The percent inhibition of mushroom tyrosinase activity can be calculated compared to non-treated controls to determine the ability of test ingredients or combinations thereof to inhibit the activity of purified enzyme. Test extract inhibition was compared with that of kojic acid (Sigma).

Cyclooxygenase (COX) Assay: An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical) can be used to analyze the effects of each of the active ingredients, any one of the combination of ingredients, or compositions having said combinations disclosed in the specification on the activity of purified cyclooxygnase enzyme (COX-1 or COX-2). According to manufacturer instructions, purified enzyme, heme and test extracts can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test extracts to inhibit the activity of purified enzyme.

Oil Control Assay: An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay: An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Moisture/Hydration Assay: Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance. Each of the active ingredients, any one of the combination of ingredients, or compositions having said combinations disclosed in the specification can be assayed according to this process.

Skin Clarity and Reduction in Freckles and Age Spots Assay: Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay: Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay: Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay With Methods Disclosed in Packman et al. (1978): Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Appearance of Lines and Wrinkles Assay with Replicas: The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and are of the replicas covered by wrinkles or fine lines was determined.

Skin Firmness Assay with a Hargens Ballistometer: Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Surface Contour of the Skin Assay with a Profilometer/Stylus Method: The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay: In other non-limiting aspects, the efficacy of each of the active ingredients, any one of the combination of ingredients, or compositions having said combinations disclosed in the specification can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing each of the active ingredients, any one of the combination of ingredients, or compositions having said combinations disclosed in the specification or with the base alone as a control. Alternatively, an untreated sample of the skin analog can be used as a control.

Production of Filaggrin: Changes in the production of filaggrin in keratinocytes due to each of the active ingredients, any one of the combination of ingredients, or compositions having said combinations disclosed in the specification can be measured. Filaggrin is the precursor to Natural Moisturizing Factor (NMF) in the skin. Increased NMF increases the moisture content of the skin. Filaggrin production in treated and non-treated keratinocytes can be determined using a bioassay that analyzes filaggrin concentration in keratinocyte cell lysates. A non-limiting example of a bioassay that can be used to quantify filaggrin production is the PROTEINSIMPLE® SIMON™ western blotting protocol. For each sample, normal human epidermal keratinocytes (NHEK) are grown in EPI-200-Mattek EPILIFE™ growth media with calcium from Life Technologies (M-EP-500-CA). NHEK are incubated in growth medium overnight at 37° C. in 5% $CO_2$ prior to treatment. NHEK are then incubated in growth medium with 1% test compound/extract or no compound/extract (negative control) for 24 to 36 hours. The NHEK can then be washed, collected, and stored on ice or colder until lysed on ice using a lysis buffer and sonication. The protein concentrations of the samples can be determined and used to normalize the samples. The lysates can be stored at −80° C. until use in the quantification assay.

The PROTEINSIMPLE® SIMON™ western blotting bioassay assay employs a quantitative western blotting immunoassay technique using an antibody specific for filaggrin to quantitatively detect filaggrin in the test samples. Cell samples are lysed and normalized for protein concentration. Normalized samples and molecular weight standards can then be loaded and ran on a denatured protein separation gel using capillary electrophoresis. The proteins in the gel are immobilized and immunoprobed using a primary antibody specific for filaggrin. The immobilized proteins can then be immunoprobed with an enzyme-linked detection antibody that binds the primary antibody. A chemiluminescent substrate solution can then be added to the immobilized proteins to allow chemiluminescent development in proportion to the amount of filaggrin bound in the immobilization. The chemiluminescent development is stopped at a specific time and the intensity of the chemiluminescent signal can be measured and compared to positive and negative controls.

Inhibition of Hyaluronidase Activity: Changes in the activity of hyaluronidase due to each of the active ingredients, any one of the combination of ingredients, or compositions having said combinations disclosed in the specification can be measured. Hyaluronidase is an enzyme that degrades HA. HA is a polysaccharide involved in stabilization of the structure of the matrix and is involved in providing turgor pressure to tissue and cells. As one non-limiting example, hyaluronidase activity can be determined using an in vitro protocol modified from Sigma-Aldrich protocol #EC 3.2.1.35. Briefly, hyaluronidase type 1-S from Sigma-Aldrich (H3506) is added to microplate reaction wells containing test compound or controls. Tannic acid can be used as a positive control inhibitor, no test compound can be added for the control enzyme, and wells with test compound or positive control but without hyaluronidase can be used as a background negative control. The wells are incubated at 37° C. for 10 minutes before addition of substrate (HA). Substrate is added and the reactions incubated at 37° C. for 45 minutes. A portion of each reaction solution is then transferred to and gently mixed in a solution of sodium acetate and acetic acid pH 3.75 to stop that portion of the reaction (stopped wells). The stopped wells and the reaction wells should both contain the same volume of solution after addition of the portion of the reaction solution to the stopped wells. Both the reaction wells and the stopped wells are incubated for 10 minutes at room temperature. Absorbance at 600 nm is then measured for both the reaction wells and the stopped wells. Inhibition can be calculated using the following formulas: Inhibitor (or control) activity= (Inhibitor stopped wells absorbance at 600 nm–inhibitor reaction wells absorbance at 600 nm); Initial activity=control enzyme absorbance at 600 nm; Percent Inhibition=[(Initial activity/Inhibitor Activity)*100]–100.

Peroxisome Proliferator-Activated Receptor Gamma (PPAR-γ) Activity: Changes in the activity of PPAR-γ due to each of the active ingredients, any one of the combination of ingredients, or compositions having said combinations disclosed in the specification can be measured. PPAR-γ is a receptor critical for the production of sebum. As one non-limiting example, the activity of PPAR-γ can be determined using a bioassay that analyzes the ability of a test compound or composition to inhibit binding of a ligand. Briefly, fluorescent small-molecule pan-PPAR ligand, FLUORMONE™ Pan-PPAR Green, available from Life Technologies (PV4894), can be used to determine if test compounds or compositions are able to inhibit binding of the ligand to PPAR-γ. The samples wells include PPAR-γ and fluorescent ligand and either: test compound or composition (test); a reference inhibitor, rosiglitazone (positive control); or no test compound (negative control). The wells are incubated for a set period of time to allow the ligand opportunity to bind the PPAR-γ. The fluorescence polarization of each sample well can then be measured and compared to the negative control well to determine the percentage of inhibition by the test compound or composition.

Cytokine Array: Human epidermal keratinocytes are cultured to 70-80% confluency. The media in the plate is aspirated and 0.025% trypsin/EDTA is added. When the cells became rounded, the culture dish is gently tapped to release the cells. The trypsin/EDTA containing cells are removed from the culture dish and neutralized. Cells are centrifuged for 5 min. at 180×g to form a pellet of cells. The supernatant is aspirated. The resulting pellet is resuspended in EPILIFE™ media (Cascade Biologics). The cells are seeded in 6-well plates at approximately 10-20% confluency. After the cells became approximately 80% confluent, the media is aspirated and 1.0 ml of EPILIFE™, along with phorbol 13-Myristate 12-acetate ("PMA") (a known inducer of inflammation) and the test composition dilutions are added to two replicate wells (i.e., 1.0% (100 µl of 100× stock) and 0.1% (10 µl of 100× stock) test compositions are diluted into a final volume of 1 ml EpiLife Growth Medium). The media is gently swirled to ensure adequate mixing. In addition, 1.0 ml of EPILIFE™ is added to the control wells, with and without additional PMA. The plates are then incubated at 37±1° C. and 5.0±1% $CO_2$ for approximately 5 hours after dosing. Following this 5-hour incubation, all media is collected in conical tubes and frozen at −70° C.

For analysis, a 16-pad hybridization chamber is attached to 16-pad FAST slides arrayed in triplicate with 16 anti-cytokine antibodies plus experimental controls (Whatman BioSciences), and the slides are placed into a FASTFrame (4 slides per frame) for processing. Arrays are blocked for 15 min. at room temp. using 70 ml S&S Protein Array Blocking buffer (Whatman Schleicher and Scheull). Blocking buffer is removed and 70 ml of each supernatant sample is added to each array. Arrays are incubated for 3 hours at room temp. with gentle agitation. Arrays are washed 3 times with TBS-T. Arrays are treated with 70 ml of an antibody cocktail, containing one biotinylated antibody corresponding to each of the arrayed capture antibodies. Arrays are incubated for 1 hour at room temp. with gentle agitation. Arrays are washed 3 times with TBS-T. Arrays are incubated with 70 ml of a solution containing streptavidin-Cy5 conjugate for 1 hour at room temp. with gentle agitation. Arrays are washed 3 times with TBS-T, quickly rinsed in de-ionized water, and dried.

Slides can be imaged in a Perkin-Elmer ScanArray 4000 confocal fluorescent imaging system. Array images can be saved and analyzed using Imaging Research ArrayVision software. Briefly, spot intensities are determined by subtracting background signal. Spot replicates from each sample condition can be averaged and then compared to the appropriate controls.

Endothelial Tube Formation: Endothelial tube formation is involved in angiogenesis and micro-vessel capillary formation. Capillary formation and angiogenesis may contribute to redness and rosacea of the skin. The ability for endothelial cells to form tubes in the presence or absence of test extracts and compounds may be determined using a capillary tubule disruption assay with pre-formed primary human umbilical vein endothelial cells (HUVEC) in a cell culture system.

Briefly, HUVECs are cultured in vitro on Extracellular Matrix, which stimulates the attachment and tubular morphogenesis of endothelial cells to form capillary-like lumen structures. These in vitro formed capillary tubules are similar to human blood vessel capillaries in many aspects. The capillary tube assay is based on this phenomenon and is used for evaluation of potential vasculature targeting agents.

HUVEC cultures are grown in a 5% $CO_2$ 37° C. cell incubator. The full growth medium for HUVECs is Endothelial Cell Basal Medium (EBM) supplemented with 2% fetal bovine serum (FBS), 12 µg/ml bovine brain extract, 1 µg/ml hydrocortisone, and 1 µg/ml GA-1000 (gentamicin-amphothericin). HUVEC cultures between passage 3 and 8 may be used for all assay experiments.

HUVECs are pre-labeled with fluorescent agent Calcein AM and seeded in Extracellular Matrix coated 96-well culture plate with their full growth medium. After about four hours of the morphogenesis process, the endothelial capillary tubes should be formed. Then, test agent in designed doses in 50 µl volume is applied into the formed capillary tubule cultures as treatment conditions. The no-treatment controls can be added with vehicle of test agents. Sutent, a FDA approved anti-angiogenic drug one concentration can be included as assay performance control. After about six hours of treatment, the endothelial tubule morphology in each well is examined by microscopy, imaged, and the capillary disrupting activities under treatment conditions can be quantitatively analyzed. Each test conditions can be conducted in duplicate wells, including controls.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Cosmetic Ingredient Dictionary, Third Edition, CTFA, 1982
2. International Cosmetic Ingredient Dictionary, Fourth edition, CTFA, 1991
3. International Cosmetic Ingredient Dictionary and Handbook, Tenth Edition, CTFA, 2004
4. International Cosmetic Ingredient Dictionary and Handbook, Twelfth Edition, CTFA, 2008
5. Harvard Health Publishing, Healthbeat, "Do retinoids really reduce wrinkles?" https://www.health.harvard.edu/staying-healthy/do-retinoids-really-reduce-wrinkles. Accessed Jul. 29, 2019.

The invention claimed is:

1. A method for topically treating skin, the method comprising applying to skin a composition comprising:
   tetrahexyldecyl ascorbate;
   *Acmella oleracea* extract; and
   retinol,
   wherein topical application of the composition treats the skin.

2. The method of claim 1, wherein the composition comprises:
   0.0001 wt. % to 5 wt. % tetrahexyldecyl ascorbate;
   0.0001 wt. % to 5 wt. % *Acmella oleracea* extract; and
   0.1 wt. % to 1.0 wt. % retinol.

3. The method of claim 1, wherein:
   *Acmella oleracea* extract is a hydroethanolic flower, leaf, or stem extract or is an extract of dried flower, stem, or leaf.

4. The method of claim 1, wherein the composition is an emulsion.

5. The method of claim 1, wherein the composition is an oil-in-water emulsion.

6. The method of claim 1, wherein the composition is a gel.

7. The method of claim 1, wherein the composition is a serum.

8. The method of claim 1, wherein the composition is an aqueous solution or an aqueous-alcoholic solution.

9. The method of claim 1, wherein the composition is applied to a fine line or wrinkle on the skin, and wherein application of the composition reduces the appearance of the fine line or wrinkle.

10. The method of claim 1, wherein the composition is applied to reddened or erythemic skin, and wherein application of the composition reduces the appearance of the reddened or erythemic skin.

11. The method of claim 1, wherein the composition is applied to skin having uneven skin tone, and wherein the composition reduces the appearance of the uneven skin tone.

12. The method of claim 1, wherein topical application of the composition to the skin increases skin firmness.

13. The method of claim 1, wherein topical application of the composition to the skin increases collagen expression in the skin.

14. The method of claim 1, wherein topical application of the composition to the skin reduces matrix metalloproteinase 1, 3, or 9 activity in the skin.

* * * * *